United States Patent
Zhang

(10) Patent No.: US 11,540,993 B2
(45) Date of Patent: Jan. 3, 2023

(54) SELF-ASSEMBLED AMINO ACID SUPRAMOLECULAR POLYMER, PREPARATION METHOD THEREFOR, AND APPLICATION THEREOF

(71) Applicant: SUZHOU OULIT BIOPHARM CO., LTD, Jiangsu (CN)

(72) Inventor: Jian Zhang, Suzhou (CN)

(73) Assignee: SUZHOU OULIT BIOPHARM CO., LTD, Jiangsu (CN)

( * ) Notice: Subject to any disclaimer, the term of this patent is extended or adjusted under 35 U.S.C. 154(b) by 55 days.

(21) Appl. No.: 16/972,465

(22) PCT Filed: Jun. 3, 2019

(86) PCT No.: PCT/CN2019/089819
§ 371 (c)(1),
(2) Date: Dec. 4, 2020

(87) PCT Pub. No.: WO2019/233377
PCT Pub. Date: Dec. 12, 2019

(65) Prior Publication Data
US 2021/0236405 A1    Aug. 5, 2021

(30) Foreign Application Priority Data

Jun. 4, 2018 (CN) .......................... 201810562174.5
Jun. 4, 2018 (CN) .......................... 201810562197.6
Jun. 4, 2018 (CN) .......................... 201810562200.4

(51) Int. Cl.
*A61K 8/64* (2006.01)
*A61K 8/02* (2006.01)
(Continued)

(52) U.S. Cl.
CPC .............. *A61K 8/64* (2013.01); *A61K 8/0241* (2013.01); *A61K 8/044* (2013.01); *A61K 8/92* (2013.01);
(Continued)

(58) Field of Classification Search
CPC ........ A61K 8/0241; A61K 8/044; A61K 8/44; A61K 8/64; A61K 8/92; A61K 8/922;
(Continued)

(56) References Cited

U.S. PATENT DOCUMENTS

| 6,090,250 A | 7/2000 | Mazzeo et al. |
| 8,697,614 B2 | 4/2014 | Choban et al. |
| 2012/0035108 A1 | 2/2012 | Miyamoto et al. |

FOREIGN PATENT DOCUMENTS

| CN | 1798821 A | 7/2006 |
| CN | 103126921 A | 6/2013 |

(Continued)

OTHER PUBLICATIONS

JP07188694 A machine translation (Hattori Tatsuya; Sano Keigo; Yoshihara Hideki) 1995(patent).[online][retrieved on Sep. 18, 2022], Retrieved from Espacenet (https://worldwide.espacenet.com/patent/search/family/018284140/publication/JPH07188694A?q=JP3296062) (Year: 1995).*

(Continued)

*Primary Examiner* — Adam C Milligan
*Assistant Examiner* — Amanda Michelle Petritsch
(74) *Attorney, Agent, or Firm* — Medler Ferro Woodhouse Mills PLLC

(57) ABSTRACT

Disclosed are a novel self-assembled amino acid supramolecular polymer, a preparation method therefor, and an application thereof. The self-assembled supramolecular polymer is N-lauroyl-L-alanyl-L-alanine or a salt thereof, and the salt thereof comprises sodium N-lauroyl-L-alanyl- (Continued)

L-alaninate and potassium N-lauroyl-L-alanyl-L-alaninate. The disclosed polymer is more effective at inhibiting bacteria and removing pesticides, and can be widely applied to the daily chemical, agricultural, and pharmaceutical industries. Further disclosed are three methods for preparing the compound. The methods produce products in high yields and are suitable for industrial production.

18 Claims, 8 Drawing Sheets

(51) Int. Cl.
  *A61K 8/04*    (2006.01)
  *A61K 8/92*    (2006.01)
  *A61Q 11/00*   (2006.01)
  *A61Q 19/00*   (2006.01)
  *C07K 1/107*   (2006.01)
  *C07K 5/062*   (2006.01)
  *C08G 69/10*   (2006.01)
  *C11D 1/10*    (2006.01)
  *A61K 8/9717*   (2017.01)

(52) U.S. Cl.
  CPC ............. *A61K 8/922* (2013.01); *A61K 8/925* (2013.01); *A61K 8/9717* (2017.08); *A61Q 11/00* (2013.01); *A61Q 19/00* (2013.01); *C07K 1/1077* (2013.01); *C07K 5/06026* (2013.01); *C08G 69/10* (2013.01); *C11D 1/10* (2013.01); *A61K 2800/30* (2013.01); *A61K 2800/412* (2013.01); *A61K 2800/48* (2013.01); *A61K 2800/524* (2013.01)

(58) Field of Classification Search
  CPC .. A61K 8/925; A61K 8/9717; A61K 2800/10; A61K 2800/30; A61K 2800/412; A61K 2800/48; A61K 2800/524; A61P 1/02; A61Q 11/00; A61Q 19/00; C08G 69/10; C11D 1/10
  See application file for complete search history.

(56) References Cited

FOREIGN PATENT DOCUMENTS

| | | | |
|---|---|---|---|
| CN | 103130675 A | 6/2013 | |
| CN | 106118914 A | 11/2016 | |
| CN | 107260563 A | 10/2017 | |
| CN | 108451783 A | 8/2018 | |
| CN | 108653025 A | 10/2018 | |
| CN | 108752228 A | 11/2018 | |
| CN | 108752420 A | 11/2018 | |
| EP | 1609836 A1 | 12/2005 | |
| EP | 2319894 A1 | 5/2011 | |
| JP | 07188694 | * 7/1995 | |
| JP | 11349932 A | * 12/1999 | |
| JP | 2004-331568 A | 11/2004 | |
| JP | 2004331568 A | * 11/2004 | ............... A61K 8/55 |
| JP | 2008303183 A | * 12/2008 | |
| WO | WO-9920237 A1 | * 4/1999 | ............. A61K 33/42 |
| WO | 2018/006734 A | 1/2018 | |

OTHER PUBLICATIONS

Restriction Requirement issued in U.S. Appl. No. 16/972,461, dated Mar. 31, 2022.
Sivaramakrishna et al., "Self-assembly, supramolecular organization, and phase transitions of a homologous series of N-acyl-L-alanines (n=8-20)," Colloids and Surfaces A: PhysiochemEng Aspects 471:108-116 (2015).
Radley and Tracey, "A Laser Diffraction and Nuclear Magnetic Resonance Investigation of the Cholesteric Potassium N-dodecanoylalaninate Mesophase System," Canadian Journal of Chemistry 63(1):95-99 (1985).
Luo et al., Self-assembled Organogels Foimed by Mono-chain L-alanine Derivatives, Chemical Communications (17):1556-1557 (2001).
Bhattachary et al., "First Report of Phase Selective Gelation of Oil from Oil/Water Mixtures. Possible Implications toward Containing Oil Spills," Chem. Commun. 185-186 (2001), DOI: 10.1039/b007848o.
Liu et al., "Research situation for phase-selective supramolecular oil gelators," Petrochemical Technology 43(12):1464-1472 (2014).
Pal et al., "Molecular mechanism of physical gelation of hydrocarbons by fatty acid amides of natural amino acids," Tetrahedron 63(31):7334-7348 (2007).
English Translation of the International Search Report in PCT/CN2019/089816, dated Sep. 2, 2019.
English Translation of the International Search Report in PCT/CN2019/089819, dated Sep. 2, 2019.
Non-Final Office Action issued in U.S. Appl. No. 16/972,461, dated May 26, 2022.

\* cited by examiner (1)

(2)

(1)

(2)

(1)

(2)

(3)

(1)

(2)

(3)

SELF-ASSEMBLED AMINO ACID SUPRAMOLECULAR POLYMER, PREPARATION METHOD THEREFOR, AND APPLICATION THEREOF

TECHNICAL FIELD

The present disclosure pertains to the technical field of preparation of amino acid type surfactants, and particularly relates to a method for preparing a novel self-assembled amino acid supramolecular polymer and application thereof.

BACKGROUND ART

Surfactants are indispensable for many fields such as daily chemical industry, agriculture, pharmaceutical industry, etc. There are dozens of surfactants currently used in the market, but the main surfactants that are commonly used include sodium dodecylbenzene sulfonate (SLS), sodium laureth sulfate (AES) and sodium lauryl sulfate (K12). While these three major surfactants have been used for decades or even over a hundred years, their negative effects in use have gradually emerged, and their impact on human safety and the environment is frequently reported.

Among other surfactants, there may be mentioned, for example, sugar alkyl glycosides (APG), and amino acid surfactants, such as lauroyl-L-glutamic acid, lauroyl glycine, lauroyl sarcosine and the like. They are biomass based surfactants with high safety, good biodegradability and excellent skin feel, and thus have attracted more and more attention. However, because of the poor detergent power of this type of surfactants, they are rarely used alone as primary surfactants; instead, they often need to be used in conjunction with other primary surfactants. Hence, the troublesome problems caused by the primary surfactants used as daily chemicals in terms of safety and biodegradability haven't been solved fundamentally.

A self-assembled N-lauroyl-L-alanine polymer may be formed in the presence of a certain amount of lauric acid, but the polymer cannot be obtained by previous patent methods. The effect of the polymer is better than that of the compounds obtained by the patent methods. Therefore, a self-assembled N-lauroyl-L-alanyl-L-alanine supramolecular polymer is prepared according to the present disclosure.

The self-assembled N-lauroyl-L-alanyl-L-alanine supramolecular polymer is a novel self-assembled amino acid supramolecular polymer synthesized on the basis of in-depth research on N-lauroyl-L-alanine, and it has the basic properties of N-lauroyl-L-alanine. However, because it has an extra group of hydrogen bonds, the whole structure is more stable and not easy to split. In addition, it comprises one more L-alanine moiety which makes the whole chain longer, similar to the length of stearic acid. It has a stronger ability to combine with oil than N-lauroyl-L-alanine. The resulting ring has a larger space which can encapsulate more organic molecular compounds and biological materials, thereby changing some physical and chemical properties of the encapsulated substances. Since N-lauroyl-L-alanyl-L-alanine itself is derived from biological materials, it has natural safety and biodegradability. Hence, it is expected to be used more widely and change the living environment of human beings greatly.

The sodium salt of the self-assembled N-lauroyl-L-alanyl-L-alanine supramolecular polymer has two groups of hydrogen bonds, so it can form a two-dimensional planar structure which has stronger structural connectivity. The resulting network structure is not easy to break. Furthermore, a single molecule includes an additional L-alanine moiety, so that the chain of the single molecule is longer, similar to the length of the eighteen-carbon sodium stearate. Therefore, it has stronger detergent power and encapsulating capacity.

SUMMARY

In order to obtain a surfactant with good biodegradability and strong detergent power, a novel self-assembled amino acid supramolecular polymer on the basis of the research on N-lauroyl-L-alanine. Compared with the existing surfactants including N-lauroyl-L-alanine, this compound exhibits more effective decontamination and antibacterial properties, very suitable for use in the daily chemical industry, agriculture, pharmaceutical industry and the like.

The following technical solution is employed to achieve the object of the present disclosure and solve its technical problem. The novel self-assembled amino acid supramolecular polymer provided according to the present disclosure has the following structure:

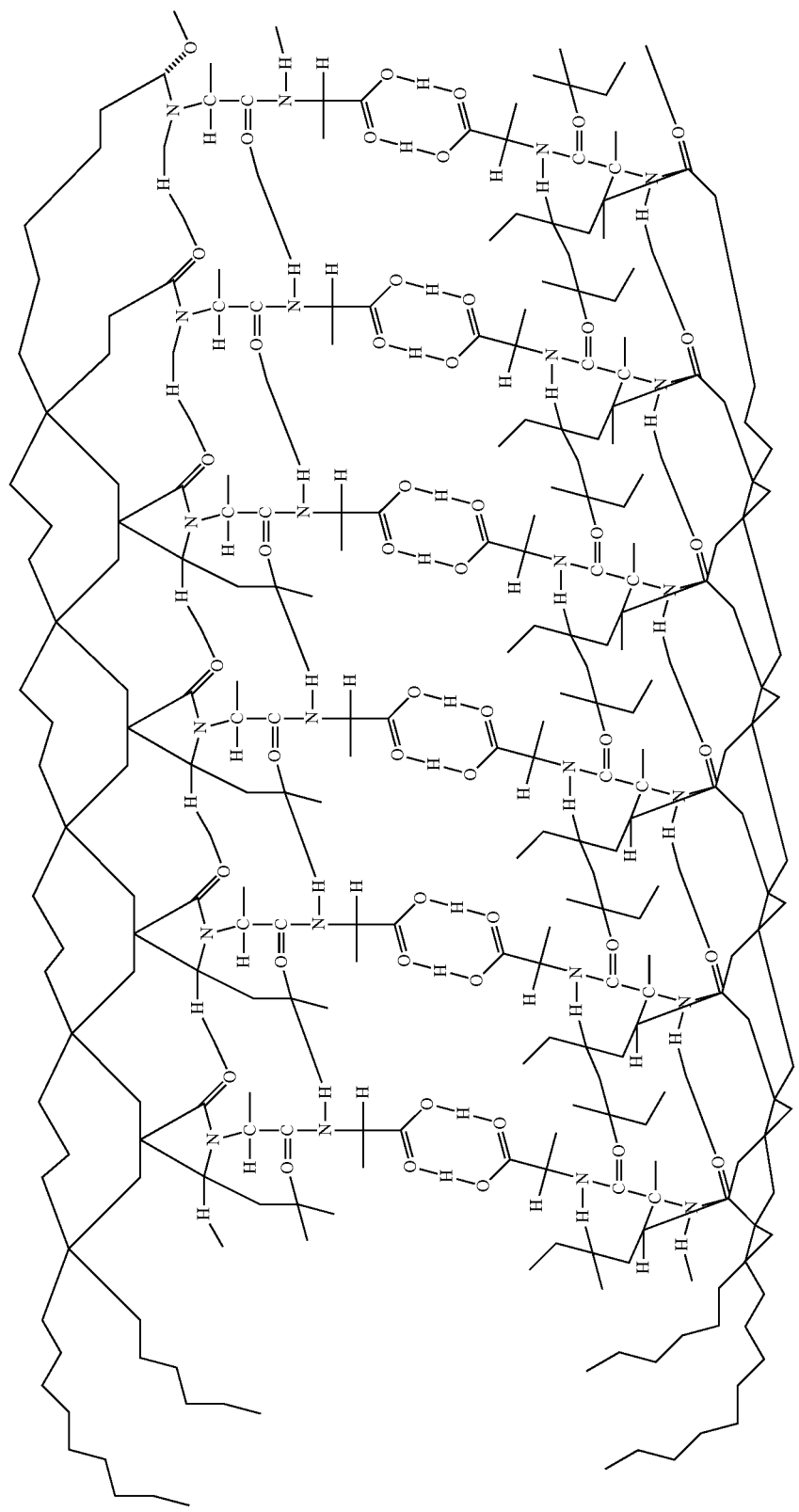

A monomer of the novel self-assembled amino acid supramolecular polymer has the following structure:

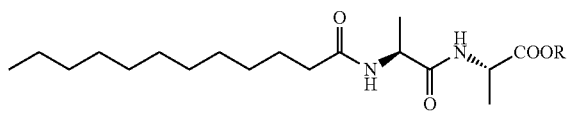

wherein R is selected from H, Na or K.

The present disclosure further relates to a novel self-assembled amino acid supramolecular polymer, comprising N-lauroyl-L-alanyl-L-alanine as a basic unit which self-assembles into a supramolecular polymer through hydrogen bonds, wherein the supramolecular polymer has a weight average molecular weight of between 5000 and 5,000,000.

The polymer is substantially free of lauric acid, wherein "substantially free" means that lauric acid is undetectable by HPLC.

The present disclosure further relates to sodium salt of a novel self-assembled amino acid supramolecular polymer having the following structure:

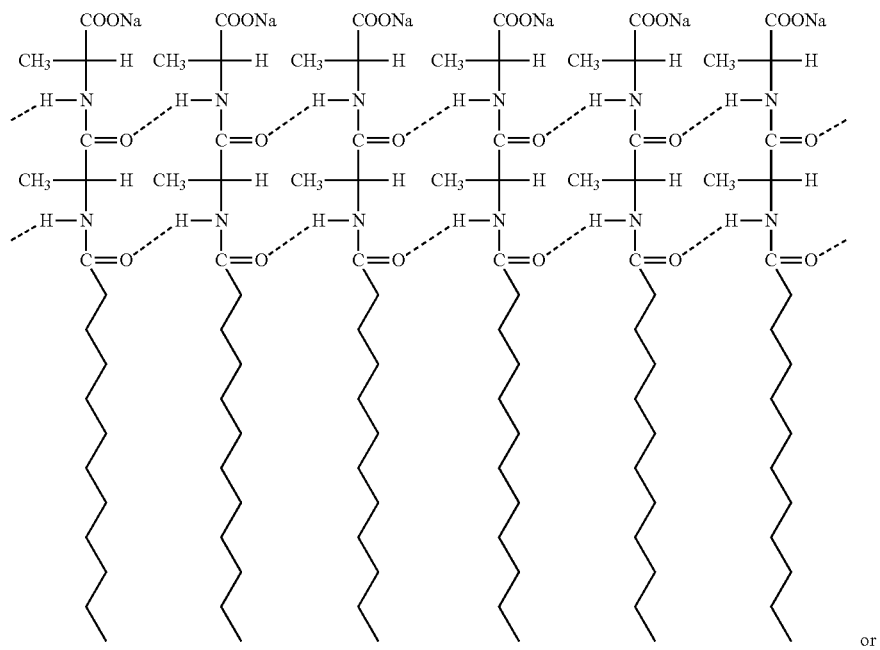

or

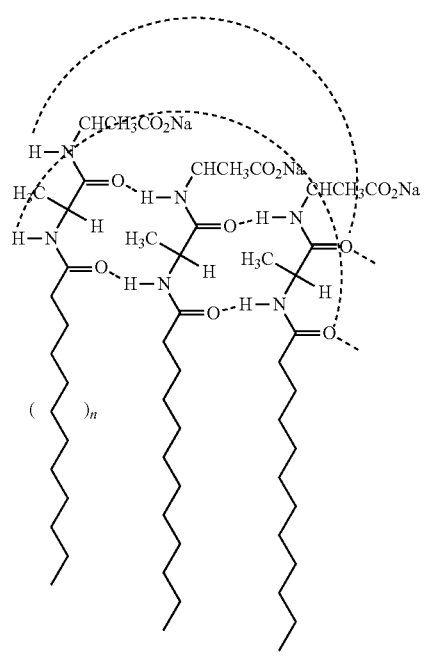

wherein n represents the number of sodium N-lauroyl-L-alanyl-L-alanine molecules forming the self-assembled supramolecular polymer.

The present disclosure further discloses sodium salt of a novel self-assembled amino acid supramolecular polymer, comprising sodium N-lauroyl-L-alanyl-L-alanine as a basic unit which self-assembles into a supramolecular polymer through hydrogen bonds, wherein the supramolecular polymer has a weight average molecular weight of between 5000 and 5,000,000.

The following technical solution is further employed to achieve the object of the present disclosure and solve its technical problem. According to the present disclosure, there is provided a method for preparing the aforementioned compound as follows:

Adding a solvent, L-alanyl-L-alanine and a catalyst to a crude N-lauroyl-L-alanyl-L-alanine product, stirring under certain conditions, cooling, filtering, washing the resulting solid, and drying to obtain a self-assembled N-lauroyl-L-alanyl-L-alanine polymer.

In the aforementioned method according to the present disclosure, the solvent is selected from acetone, methanol, ethanol, acetonitrile, tetrahydrofuran, or mixed solvents made from one or more of the above solvents with water.

In the aforementioned method according to the present disclosure, the catalyst is selected from one or more of sulfuric acid, p-toluenesulfonic acid, and emulsifiers.

In the aforementioned method according to the present disclosure, a molar ratio of the crude N-lauroyl-L-alanyl-L-alanine product, solvent, L-alanyl-L-alanine, and catalyst is 1:(5-10):(0.1-0.2):(0.001-0.1).

In the aforementioned method according to the present disclosure, the stirring conditions include: temperature 25-100° C., pressure 5 kg-50 kg, time 1-3 h.

The crude N-lauroyl-L-alanyl-L-alanine is prepared by a method comprising the following steps:

(1) Dissolving L-alanyl-L-alanine and a metallic inorganic base in a mixed solution of distilled water and an organic solvent, and stirring uniformly to obtain an L-alanyl-L-alanine salt solution;

(2) Adding lauroyl chloride and a metallic inorganic base in sequence to the L-alanyl-L-alanine salt solution obtained above, and then continuing the stirring under certain conditions to obtain a pasty N-lauroyl-L-alanyl-L-alanine salt;

(3) Acidifying the pasty N-lauroyl-L-alanyl-L-alanine salt obtained above to precipitate a white solid gradually, cooling and then filtering to obtain the crude N-lauroyl-L-alanyl-L-alanine product.

In the aforementioned method according to the present disclosure, a molar ratio of the L-alanyl-L-alanine to the metallic inorganic base in Step (1) is 1:(1-1.5).

In the aforementioned method according to the present disclosure, the metallic inorganic base in Step (1) is selected from one or more of sodium hydroxide, potassium hydroxide, sodium carbonate, and potassium carbonate.

In the aforementioned method according to the present disclosure, the organic solvent in Step (1) is selected from one or more of acetone, methanol, ethanol, acetonitrile, and tetrahydrofuran.

In the aforementioned method according to the present disclosure, a volume ratio of the distilled water to the organic solvent in Step (1) is 1:(1-1.5).

In the aforementioned method according to the present disclosure, a feeding molar ratio of the lauroyl chloride to the L-alanyl-L-alanine in Step (2) is (0.8-1):1.

In the aforementioned method according to the present disclosure, the stirring conditions in Step (2) include: temperature 5-50° C., time 1-3 h.

In the aforementioned method according to the present disclosure, the metallic inorganic base in Step (2) has a concentration of 30-80%.

In the aforementioned method according to the present disclosure, the metallic inorganic base in Step (2) is selected from one or more of sodium hydroxide, potassium hydroxide, sodium carbonate, and potassium carbonate.

The following technical solution is further employed to achieve the object of the present disclosure and solve its technical problem. According to the present disclosure, there is provided a method for preparing the aforementioned compound, comprising the following steps:

(1) Mixing and reacting N-lauroyl-L-alanine and a chlorinating reagent, cooling, adding pentan-2-one and activated carbon, conducting decolorization, filtration and reduced pressure distillation in sequence, going on to add an organic solvent to dissolve the acyl chloride in N-lauroyl-L-alanine to obtain a N-lauroyl-L-alanyl chloride solution;

(2) Dissolving L-alanine and a metallic inorganic base in a mixed solution of distilled water and an organic solvent, and stirring uniformly to obtain an L-alanine salt solution;

(3) Adding the solution of N-lauroyl-L-alanyl chloride in acetone obtained in Step (1) and a metallic inorganic base to the L-alanine salt solution obtained above, and then continuing the stirring under certain conditions to obtain a pasty N-lauroyl-L-alanyl-L-alanine salt;

(4) Acidifying the pasty N-lauroyl-L-alanyl-L-alanine salt obtained above to precipitate a white solid gradually, cooling and then filtering to obtain the crude N-lauroyl-L-alanyl-L-alanine product;

(5) Adding a solvent, L-alanyl-L-alanine and a catalyst to the crude N-lauroyl-L-alanyl-L-alanine product, stirring under certain conditions, cooling, filtering, washing the resulting solid, and drying to obtain a self-assembled N-lauroyl-L-alanyl-L-alanine supramolecular polymer.

In Step (1) of the aforementioned method according to the present disclosure, pentan-2-one is added in an amount of 80-100 mL; activated carbon is added in an amount of 1-3 g; and the organic solvent is added in an amount of 80-100 mL.

In the aforementioned method according to the present disclosure, in Step (1), a molar ratio of the N-lauroyl-L-alanine to the chlorinating agent is (1-1.5):5, and the chlorinating agent may be one or more of thionyl chloride, phosphorus trichloride, triphosgene, and N-chlorosuccinimide.

In the aforementioned method according to the present disclosure, a molar ratio of the L-alanine to the metallic inorganic base in Step (2) is 1:(1-1.5).

In the aforementioned method according to the present disclosure, the metallic inorganic base in Step (2) is selected from one or more of sodium hydroxide, potassium hydroxide, sodium carbonate, and potassium carbonate.

In the aforementioned method according to the present disclosure, the organic solvent in Step (2) is selected from one or more of acetone, methanol, ethanol, acetonitrile, and tetrahydrofuran.

In the aforementioned method according to the present disclosure, a volume ratio of the distilled water to the organic solvent in Step (2) is 1:(1-1.5).

In the aforementioned method according to the present disclosure, a feeding molar ratio of the solution of N-lauroyl-L-alanyl chloride in acetone in Step (3) to L-alanine is (0.8-1):1.

In the aforementioned method according to the present disclosure, the stirring conditions in Step (3) include: temperature 5-50° C., time 1-3 h.

In the aforementioned method according to the present disclosure, the metallic inorganic base in Step (3) has a concentration of 30-80%.

In the aforementioned method according to the present disclosure, the metallic inorganic base in Step (3) is selected from one or more of sodium hydroxide, potassium hydroxide, sodium carbonate, and potassium carbonate.

The following technical solution is further employed to achieve the object of the present disclosure and solve its technical problem. According to the present disclosure, there is provided use of the compound obtained by the aforementioned preparation method as a surfactant used in the fields of daily chemicals, agriculture, and pharmaceutical industry.

The following technical solution is further employed to achieve the object of the present disclosure and solve its technical problem. According to the present disclosure, there is provided use of the aforementioned compound as a surfactant used in the fields of daily chemicals, agriculture, and pharmaceutical industry.

The following technical solution is further employed to achieve the object of the present disclosure and solve its technical problem. According to the present disclosure, there is provided a supramolecular amino acid, wherein the supramolecular amino acid is formed by hydrogen bonding the N-lauroyl-L-alanyl-L-alanine monomers obtained by the aforementioned preparation method.

The present disclosure has the following beneficial technical effects in comparison with the prior art:

1. The novel self-assembled amino acid supramolecular polymer according to the present disclosure is prepared by a method consisting of simple process steps. It is formed by condensation of natural lauric acid and natural L-alanyl-L-alanine. It exists stably under ambient conditions, and is non-toxic and harmless to human body. Even if it enters human body, it will quickly degrade into lauric acid and L-alanine naturally, and the degradation products are natural materials that can be recycled. Furthermore, the reaction conditions are mild, and thus appropriate for industrial production.

2. The weight percentage of lauric acid in the self-assembled supramolecular N-lauroyl-L-alanyl-L-alanine prepared according to the inventive method is between 0.0001% and 0.02%, substantially free of lauric acid. Thus, the content of lauric acid has no influence on the structure or properties of N-lauroyl-L-alanyl-L-alanine, thereby effectively avoiding the influence of lauric acid on product quality.

3. The self-assembled supramolecular N-lauroyl-L-alanyl-L-alanine obtained by the inventive method has a three-dimensional network structure which strongly facilitates adsorption of oil and other organics. In use, the pH is 6-7, which is more suitable for the pH requirement of human body. At least 90% of the compound exists in the form of sodium salt, and the rest exists in the form of acid. They coexist in two dimensions and three dimensions, providing strong abilities for cleaning and for adsorption of bacteria, pesticides, odor, etc.

4. The self-assembled supramolecular N-lauroyl-L-alanyl-L-alanine prepared by the inventive method has a stable structure and stable properties, and it also possesses supramolecular properties. Due to the existence of various gelling factors in the solution containing the molecules, such as hydrogen bond, electrostatic force, hydrophobic force, and π-π interaction, the liquid components are driven to stand still. An amino acid having a three-dimensional network spatial structure is thus formed. As such, the compound is imparted with the abilities for physical sterilization, odor removal, and pesticide residue removal. It has a sound bacteriostatic rate, and it is able to inhibit *Escherichia coli, Staphylococcus aureus, Candida albicans* and *Pseudomonas aeruginosa* each at a bacteriostatic rate up to 100%. It can remove pesticide residue effectively. The removal rate for methamidophos can reach 90.6%, and the removal rate for acephate can reach 93.2%. It also has good deodorizing performance.

5. The novel self-assembled amino acid supramolecular polymer prepared by the inventive method exists in the form of countless columnar bodies with huge gap between the molecules. The huge gap can entrap organic substances such as drug molecules, pesticide residue and tiny inorganic particles. For applications in the pharmaceutical field, N-lauroyl-L-alanyl-L-alanine can encapsulate drug molecules, and act as a slow release agent, such that the active ingredients of a drug can be released slowly under the action of an enzyme. For applications in the pesticide field, N-lauroyl-L-alanyl-L-alanine can encapsulate a pesticide to prevent the pesticide from penetrating and entering the interior of a plant. For applications in the field of cosmetics, a combination of N-lauroyl-L-alanyl-L-alanine and a natural oil may modify the physical properties of the oil, such that the modified natural oil is close to the oil secreted by human body, and thus provides good experience to consumers. N-lauroyl-L-alanyl-L-alanine can encapsulate a cosmetic active material, so that the active material will not be easily oxidized or deactivated, and particles of the cosmetic active material can be dispersed uniformly and suspended in a cosmetic system.

DETAILED DESCRIPTION

After extensive and intensive research, the present inventors have discovered a peculiar method that can be used to form a polymer substantially free or free of lauric acid by self-assembly of N-lauroyl-L-alanyl-L-alanine monomer via hydrogen bonding, and an elastic void-containing structure can be formed. This structure can immobilize oily substances. When the polymer forms a salt with a base, the resulting polymer salt may be used as a surfactant. The invention is accomplished on such a basis.

Figure 7:
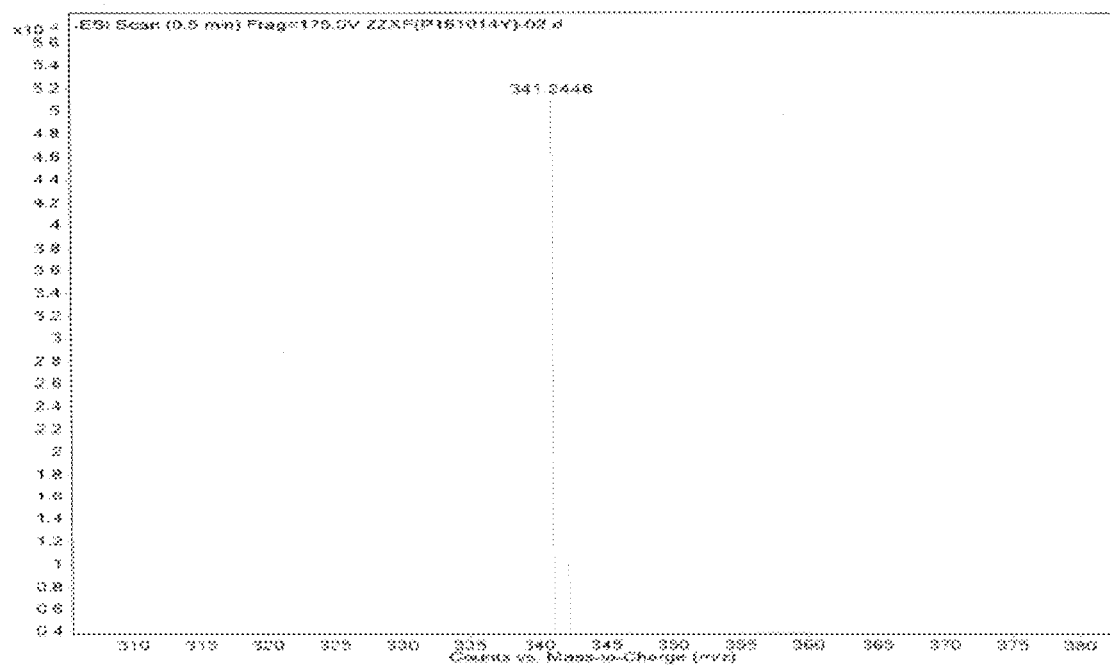
FIG. 7 shows a mass spectrum of the self-assembled N-lauroyl-L-alanyl-L-alanine polymer obtained according to the synthetic method in Example 1 in the present disclosure, wherein Counts vs Mass-to-Chorge (m/z)
Sample Name: ZZXF (P161014Y)
Inj Vol: injection volume
Data filename: ZZXF (P161014Y)-02.d
Position: position
Injposition: injection position
ACQ method: ACQ method
Instrument Name: instrument name
Sample Type: sample type
Comment: comment
User name: user's name
IRM Calibration Status: IRM calibration data
Acquired Time: precise time
Success: success
PM: afternoon

As used herein, "the polymer or its salt provided according to the present disclosure is substantially free or free of lauric acid" means that, for example, lauric acid cannot be detected by a high-performance liquid chromatograph (equipped with an ultraviolet detector; a chromatographic column: ODS-2HYPERSIL C18 250*4.6 mm 5 μm; a mobile phase vacuum filtration and degassing device; and a 0.45 μm organic filter membrane). That is, the content of lauric acid has no influence on the properties or structure of N-lauroyl-L-alanyl-L-alanine. Alternatively, it means that no molecular ion peak characteristic of lauric acid can be observed in the mass spectrum obtained by mass spectrometry, for example, without limitation, the mass spectrum obtained by an Agilent 1200/6220 LC/MS instrument, as shown in FIG. 7.

The N-lauroyl-L-alanyl-L-alanine salts involved in the present disclosure are sodium N-lauroyl-L-alanyl-L-alanine and/or potassium N-lauroyl-L-alanyl-L-alanine. They may also be salts formed from N-lauroyl-L-alanine with basic amino acids, such as salts formed with arginine, histidine, lysine, and the like.

Polymer or Salt Thereof

There is provided a self-assembled amino acid supramolecular polymer or a salt thereof according to the present disclosure, wherein the polymer is formed by hydrogen bonding N-lauroyl-L-alanyl-L-alanine monomers, wherein the polymer is substantially free or free of lauric acid.

The N-lauroyl-L-alanyl-L-alanine monomer or a salt thereof is a compound having the following structure:

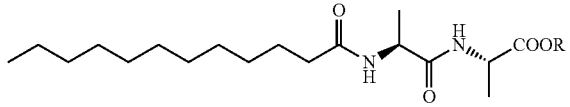

wherein R is selected from H, Na or K.

Said hydrogen bonding N-lauroyl-L-alanyl-L-alanine monomers may provide a structure as shown by Formula (I):

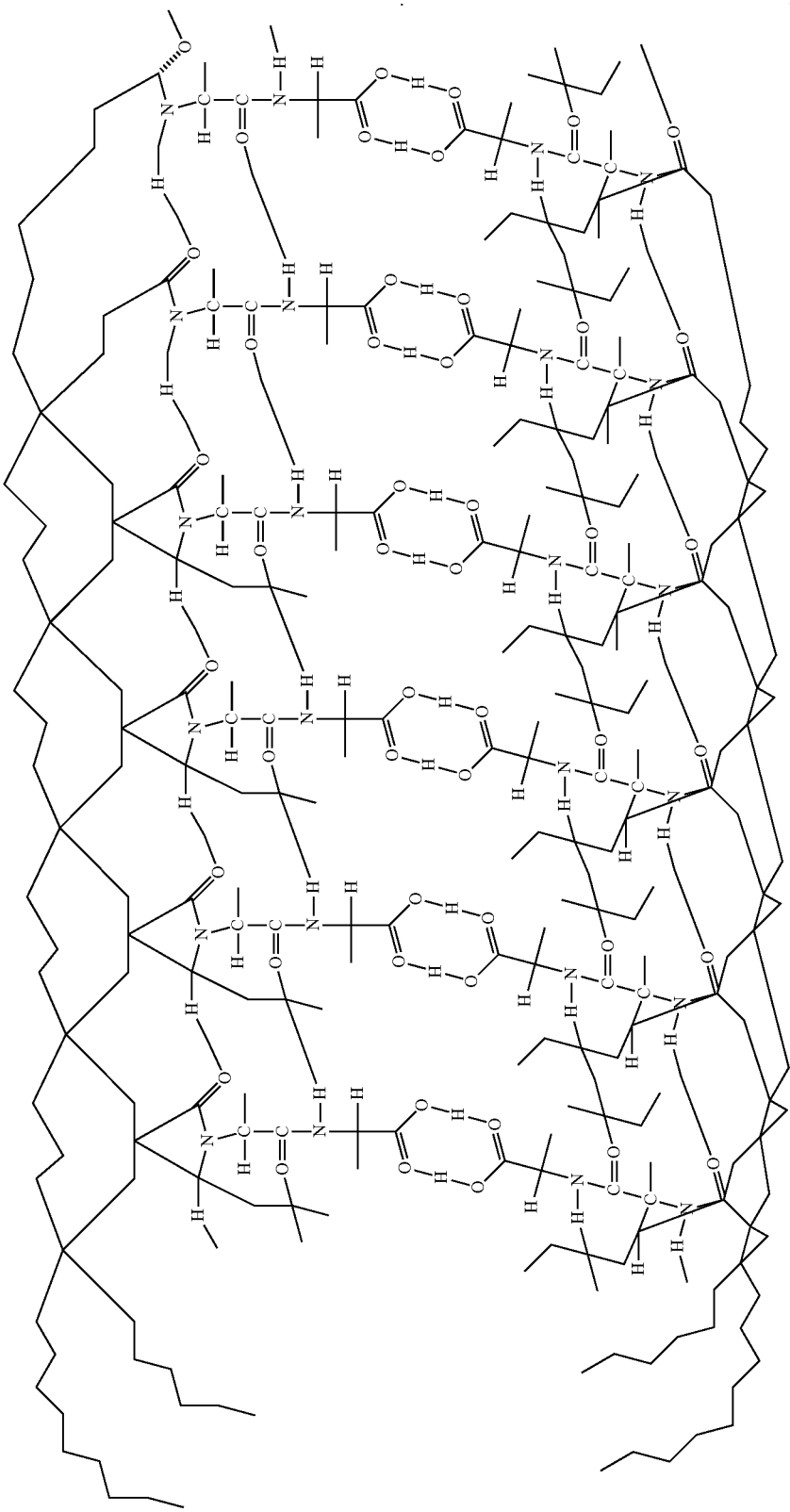

The self-assembled amino acid supramolecular polymer provided according to the present disclosure has a weight average molecular weight of between 5000 and 5,000,000, and a melting point of 148-150° C.

There is also provided a salt of the aforementioned self-assembled amino acid supramolecular polymer according to the present disclosure, wherein the salt is formed from the polymer with a base, wherein the base is selected from inorganic and organic bases.

In a preferred embodiment, the inorganic base is selected from sodium hydroxide, potassium hydroxide, or lithium hydroxide.

In a preferred embodiment, the organic base is a natural basic amino acid (arginine, lysine or histidine).

In one embodiment according to the present disclosure, there is provided a sodium salt of a self-assembled amino acid supramolecular polymer, formed by hydrogen bonding sodium N-lauroyl-L-alanyl-L-alanine monomers, wherein the sodium salt of the polymer is substantially free or free of lauric acid.

Said hydrogen bonding sodium N-lauroyl-L-alanyl-L-alanine monomers may further provide a structure as shown by Formula (II):

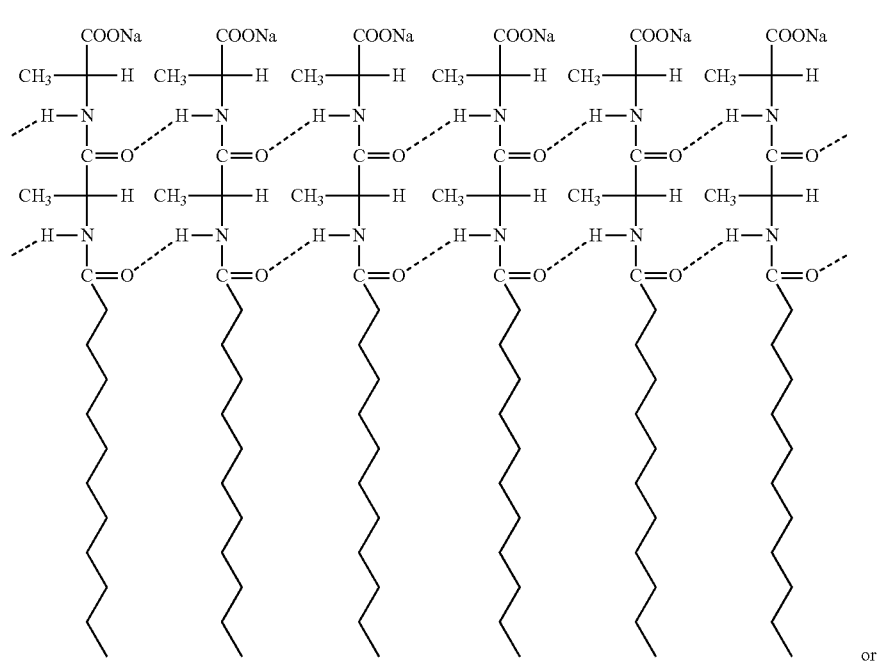

or

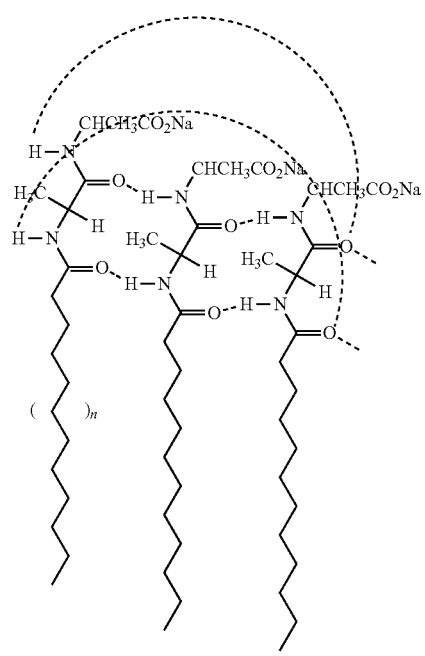

wherein n is 8-20,000; wherein n sodium N-lauroyl-L-alanyl-L-alanine molecules are linked in sequence by hydrogen bonds in the same plane, or n sodium N-lauroyl-L-alanyl-L-alanine molecules are linked in sequence by hydrogen bonds and the first and last molecules are also linked by hydrogen bonds to form a columnar structure.

The sodium salt of the self-assembled amino acid supramolecular polymer obtained above has a weight average molecular weight of between 5,000 and 5,000,000.

According to the present disclosure, there is also provided a composition comprising the self-assembled amino acid supramolecular polymer or a salt thereof provided according to the present disclosure, and a polymer formed by hydrogen bonding N-lauroyl-L-alanine monomers or a salt thereof substantially free or free of lauric acid, wherein the polymer formed by hydrogen bonding N-lauroyl-L-alanine monomers or the salt thereof accounts for 0-60 wt. % based on the total weight of the composition.

Said hydrogen bonding N-lauroyl-L-alanine monomers may provide a structure as shown by Formula (I'):

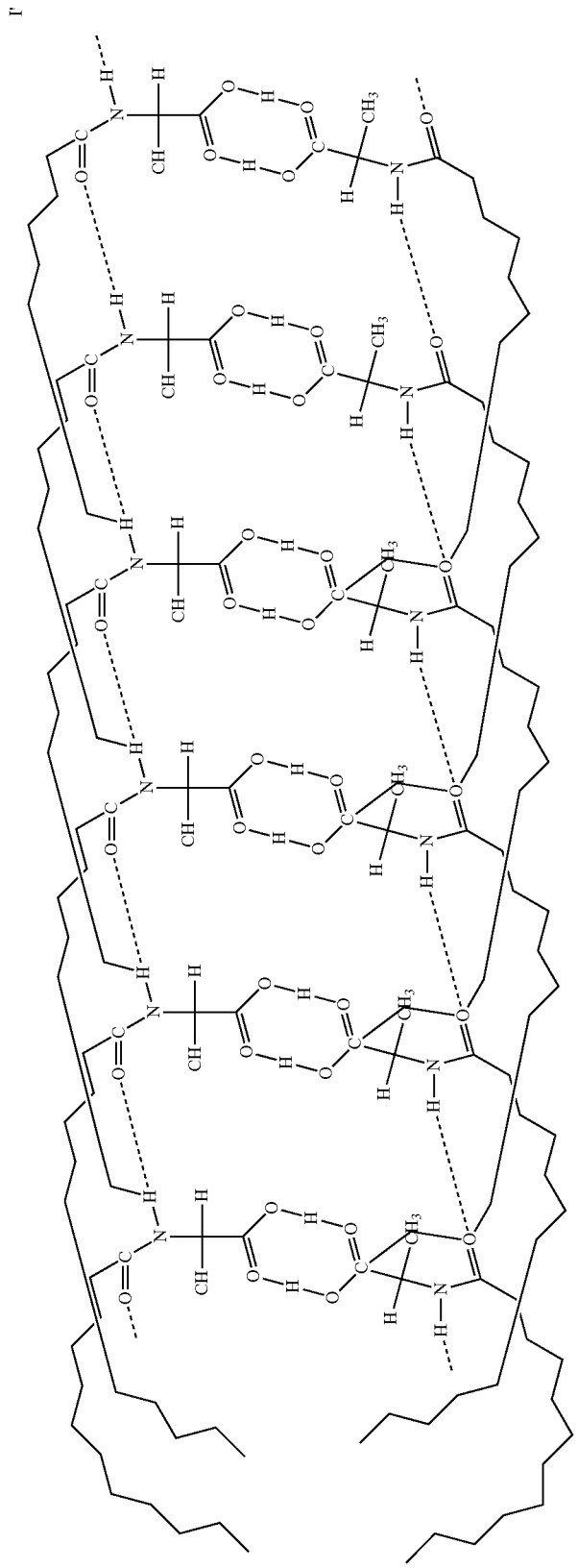

wherein its weight average molecular weight is between 2,000 and 5,000,000, and its melting point is 82-84° C.; the sodium salt of the polymer has a maximum solubility of 15 w/v %, as measured according to a solubility measuring method (Chinese Pharmacopoeia (2015 edition), General Guide). That is, the maximum amount of the self-assembled polymeric sodium N-lauroyl-L-alanine dissolved in 100 ml water is 15 grams at 25° C. and 1 atm.

Said hydrogen bonding sodium N-lauroyl-L-alanine monomers may also provide a structure as shown by Formula (II'):

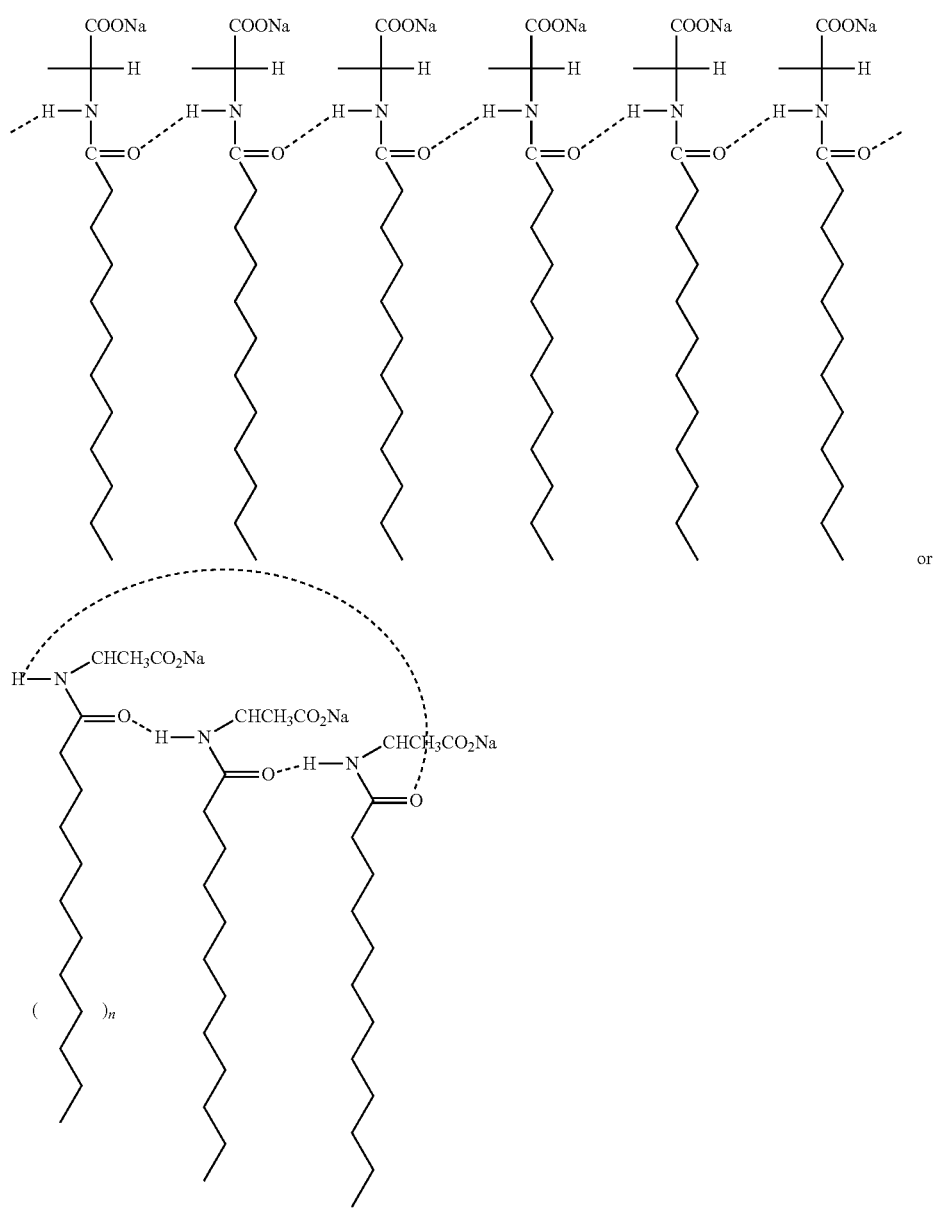

wherein n represents the number of sodium N-lauroyl-L-alanine molecules forming the self-assembled supramolecular polymer;

n sodium N-lauroyl-L-alanine molecules are linked in sequence by hydrogen bonds in the same plane, or n sodium N-lauroyl-L-alanine molecules are linked in sequence by hydrogen bonds and the first and last molecules are also linked by hydrogen bonds to form a columnar structure.

The sodium salt of the polymer shown by Formula (II') has a weight average molecular weight of between 2,800-770,000, from which it can be inferred that n ranges from 10 to 3000; and the solubility of the sodium salt in water does not exceed 15 g/100 ml.

Method for Preparing Polymer or Salt Thereof

According to the present disclosure, there is provided a method for preparing a self-assembled amino acid supramolecular polymer, comprising the following steps:

Step I, dissolving L-alanyl-L-alanine and a metallic inorganic base in a mixed solution of distilled water and an organic solvent, and stirring uniformly to obtain an L-alanyl-L-alanine salt solution;

Step II, adding lauroyl chloride and a metallic inorganic base in sequence to the L-alanyl-L-alanine salt solution obtained above to allow the reaction system to have a pH=8-10, and then continuing the stirring under certain conditions to obtain a pasty N-lauroyl-L-alanyl-L-alanine salt;

Step III, acidifying the pasty N-lauroyl-L-alanyl-L-alanine salt obtained above to a pH=3-4 to precipitate a white solid gradually, and then placing the resultant in an ice bath for 1-3 h, filtering to obtain a crude N-lauroyl-L-alanyl-L-alanine product;

Step IV, adding a solvent, L-alanyl-L-alanine and a catalyst to the crude N-lauroyl-L-alanyl-L-alanine product obtained above, and stirring under certain conditions to obtain the self-assembled amino acid supramolecular polymer provided according to the present disclosure.

In one embodiment according to the present disclosure, a volume ratio of the distilled water to the organic solvent in Step I is 1:(1-1.5).

In one embodiment according to the present disclosure, a molar ratio of the L-alanyl-L-alanine to the metallic inorganic base in Step I is 1:(1-1.5).

In one embodiment according to the present disclosure, the metallic inorganic base in Step I is selected from one or more of sodium hydroxide, potassium hydroxide, sodium carbonate, and potassium carbonate.

In one embodiment according to the present disclosure, the organic solvent in Step I is selected from one or more of acetone, methanol, ethanol, acetonitrile, and tetrahydrofuran.

In one embodiment according to the present disclosure, a feeding molar ratio of the lauroyl chloride to the L-alanyl-L-alanine in Step II is (0.8-1):1.

In one embodiment according to the present disclosure, the stirring conditions in Step II include: temperature 5-50° C., time 1-3 hours.

In one embodiment according to the present disclosure, the metallic inorganic base in Step II has a concentration of 30-80%; and the metallic inorganic base is selected from one or more of sodium hydroxide, potassium hydroxide, sodium carbonate, and potassium carbonate.

In one embodiment according to the present disclosure, in Step II, a solution of N-lauroyl-L-alanyl chloride in acetone and a metallic inorganic base are added to the L-alanyl-L-alanine salt solution obtained in Step I to allow the reaction system to have a pH=8-10, and then the stirring is continued under certain conditions to obtain a pasty N-lauroyl-L-alanyl-L-alanine salt.

In one embodiment according to the present disclosure, the solution of N-lauroyl-L-alanyl chloride in acetone is obtained as follows: N-lauroyl-L-alanine and thionyl chloride are mixed and reacted for 1-3 hours; subsequently, the excess thionyl chloride is evaporated; after cooling, pentan-2-one and activated carbon are added; decolorization, filtration, and reduced pressure distillation are conducted in sequence to take away the residual thionyl chloride; water and acetone are continued to be added to dissolve the acyl chloride in the N-lauroyl-L-alanine, so as to obtain the solution of N-lauroyl-L-alanyl chloride in acetone. The molar ratio of N-lauroyl-L-alanine to thionyl chloride is (1-1.5):5.

In one embodiment according to the present disclosure, in Step II, the resulting methyl N-lauroyl-L-alanyl-L-alanine and the metallic inorganic base are dissolved in a mixed solution of distilled water and an organic solvent to react for 4-8 hours. After the reaction is complete, the excess organic solvent is removed by evaporation to obtain a pasty N-lauroyl-L-alanyl-L-alanine salt.

In one embodiment according to the present disclosure, the feeding molar ratio of the methyl N-lauroyl-L-alanyl-L-alanine to the metallic inorganic base is 1:(1-1.5); and the metallic inorganic base is selected from one or more of sodium hydroxide, potassium hydroxide, sodium carbonate, and potassium carbonate.

In one embodiment according to the present disclosure, the volume ratio of the distilled water to the organic solvent is 1:(3-7); and the organic solvent is selected from one or more of acetone, methanol, ethanol, and acetonitrile.

In one embodiment according to the present disclosure, methyl N-lauroyl-L-alanyl-L-alanine is obtained by dissolving methyl L-alanine hydrochloride, a water-soluble organic base (selected from one or more of triethylamine, pyridine, and triethanolamine) and N-lauroyl-L-alanyl chloride in acetone, reacting under certain conditions (reacting at 0-5° C. for 3-7 hours), heating to room temperature for further reaction for 4-6 hours, and evaporating the excess acetone after the reaction is complete; and the N-lauroyl-L-alanyl chloride is obtained by dissolving N-lauroyl-L-alanine and triphosgene in chloroform, adding a small amount of a catalyst (selected from one or more of dimethylformamide, pyridine, 1-methylpyrrolidone, 1-methylpiperidine, and 1-ethylpiperidine), reacting (the volume ratio of chloroform to the catalyst being (200-300):(1-10); reacting at 30-50° C. for 4-8 hours), and then evaporating the excess chloroform, wherein the feeding molar ratio of N-lauroyl-L-alanine to triphosgene is (1-1.5): 0.3; the feeding molar ratio of methyl L-alanine hydrochloride, the water-soluble organic base and N-lauroyl-L-alanyl chloride is (0.8-1):(0.8-1):1.

In an embodiment according to the present disclosure, the hydrochloric acid in Step III has a concentration of 5-15%.

In one embodiment according to the present disclosure, the solvent in Step IV is selected from acetone, methanol, ethanol, acetonitrile, tetrahydrofuran, or mixed solvents made from one or more of the above solvents with water.

In one embodiment according to the present disclosure, the catalyst in Step IV is selected from one or more of sulfuric acid, p-toluenesulfonic acid, and emulsifiers.

In one embodiment according to the present disclosure, a mixing molar ratio of the crude N-lauroyl-L-alanyl-L-alanine product, the solvent, L-alanyl-L-alanine, and the catalyst is 1:(5-10):(0.1-0.2):(0.001-0.1).

In one embodiment according to the present disclosure, the stirring conditions in Step IV include: temperature 25-100° C., pressure 5 kg-50 kg, time 1-3 hours.

In one embodiment according to the present disclosure, in Step IV, the stirring is followed by cooling and filtering to obtain a solid which is washed and then dried to obtain a self-assembled N-lauroyl-L-alanyl-L-alanine polymer substantially free of lauric acid.

Use of Polymer or Salt Thereof

The self-assembled amino acid supramolecular polymer provided according to the present disclosure may be used to immobilize oily substances, and its salt may be used as a surfactant.

The self-assembled amino acid supramolecular polymer or its salt provided according to the present disclosure may be used widely in the fields of daily chemicals, agriculture, or pharmaceutical industry, for example, without limitation, for preparing toothpaste, skin care composition, laundry liquid, perfumed soap, laundry powder, cleanser essence, facial mask, etc.

The present disclosure will be further described below with reference to the accompanying drawings and examples. It is to be understood that these examples are only used to illustrate the present disclosure, not to limit the scope of the present disclosure. It is to be further understood that various changes or modifications to the present disclosure can be made by those skilled in the art after reading the above teachings of the present disclosure, and these equivalent variations fall in the scope defined by the accompanying claims of the application as well.

Example 1 Synthesis of Self-Assembled N-Lauroyl-L-Alanyl-L-Alanine Polymer

Embodiment 1

16.0 g (0.1 mol) L-alanyl-L-alanine and 4.0 g (0.1 mol) sodium hydroxide were dissolved in a mixed solution of 450 mL distilled water and 450 mL acetone in a 2 L three-necked flask at ambient temperature, and stirred uniformly to obtain a sodium L-alanyl-L-alanine solution.

Under the condition of 25° C., 21.9 g (0.1 mol) lauroyl chloride was added dropwise slowly to the L-alanyl-L-alanine salt solution, and then a 50% sodium hydroxide solution was added dropwise to allow the reaction system to have a pH=9. After the addition was complete, stirring was continued for 2 h at 25° C. to obtain a pasty N-lauroyl-L-alanyl-L-alanine salt.

Hydrochloric acid was added to the pasty N-lauroyl-L-alanyl-L-alanine salt to acidify it to a pH=3-4. A white solid precipitated gradually. Then, the resultant was placed in an ice bath for 2 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:7.5:0.2:0.002. Stirring was conducted for 2 h at a temperature of 60° C. and a pressure of 27 kg, so that lauric acid in a small amount was completely consumed. Then, cooling and filtering were conducted. The resulting solid was washed twice with pure water, and finally dried at 100° C. to obtain a self-assembled N-lauroyl-L-alanyl-L-alanine polymer.

Figure 1:
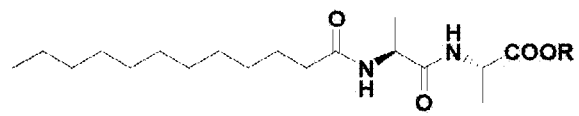
FIG. 1 shows the structure of the monomer of the inventive compound according to the present disclosure.
Figure 2A:
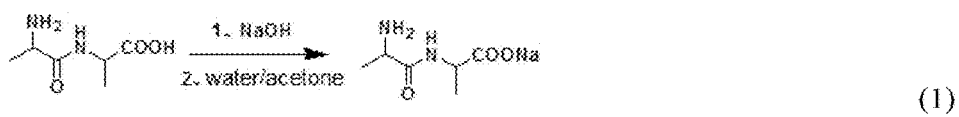
FIG. 2a shows the chemical reaction formulae for preparing the crude N-lauroyl-L-alanyl-L-alanine product according to the synthetic method in Example 1 in the present disclosure.
Figure 2A:
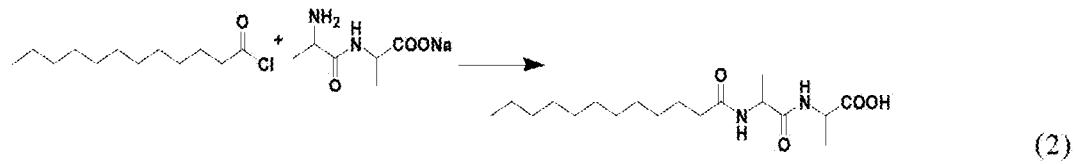
Figure 2B:
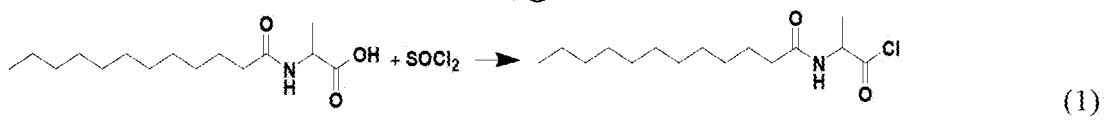
FIG. 2b shows the chemical reaction formulae for preparing the crude N-lauroyl-L-alanyl-L-alanine product according to the synthetic method in Example 4 in the present disclosure.
Figure 2B:
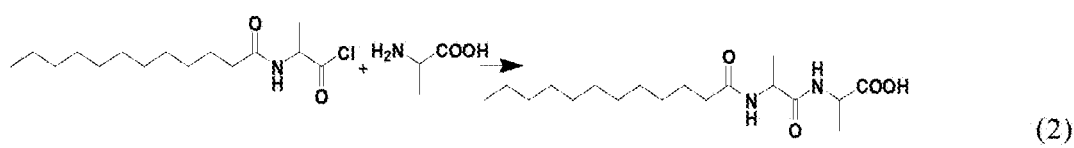
Figure 2C:
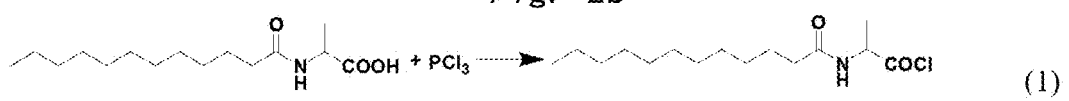
FIG. 2c shows the chemical reaction formulae for preparing the crude N-lauroyl-L-alanyl-L-alanine product according to the synthetic method in Example 5 in the present disclosure.
Figure 2C:
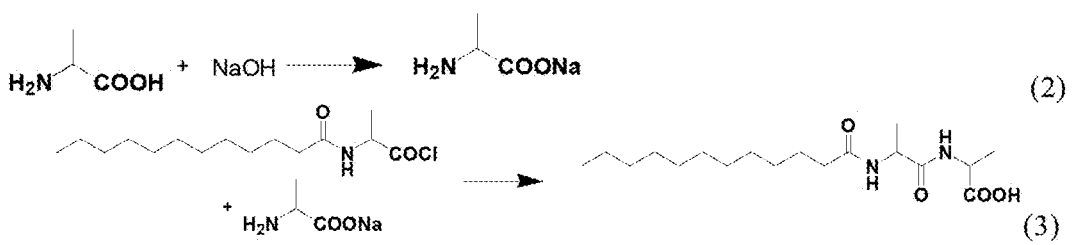
Figure 2D:
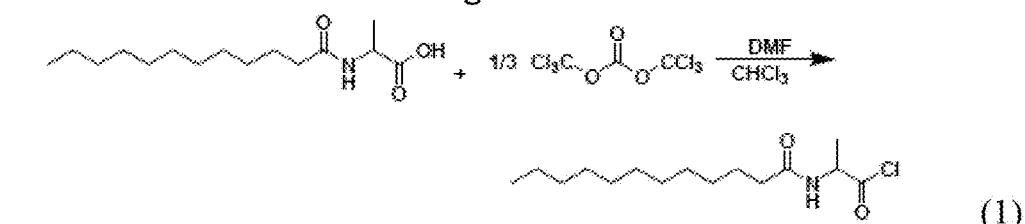
FIG. 2d shows the chemical reaction formulae for preparing the crude N-lauroyl-L-alanyl-L-alanine product according to the synthetic method in Example 7 in the present disclosure.
Figure 2D:
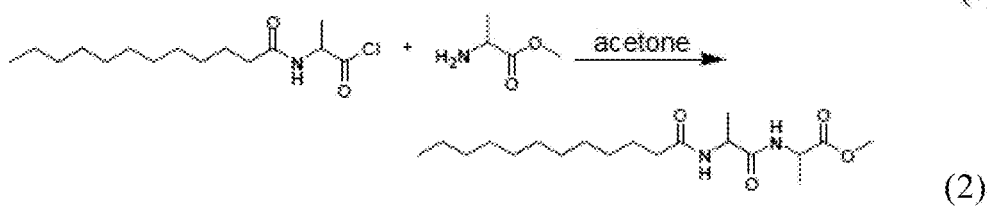
Figure 2D:
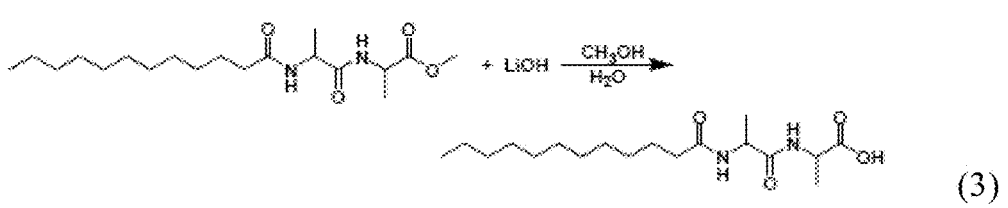
Figure 3:
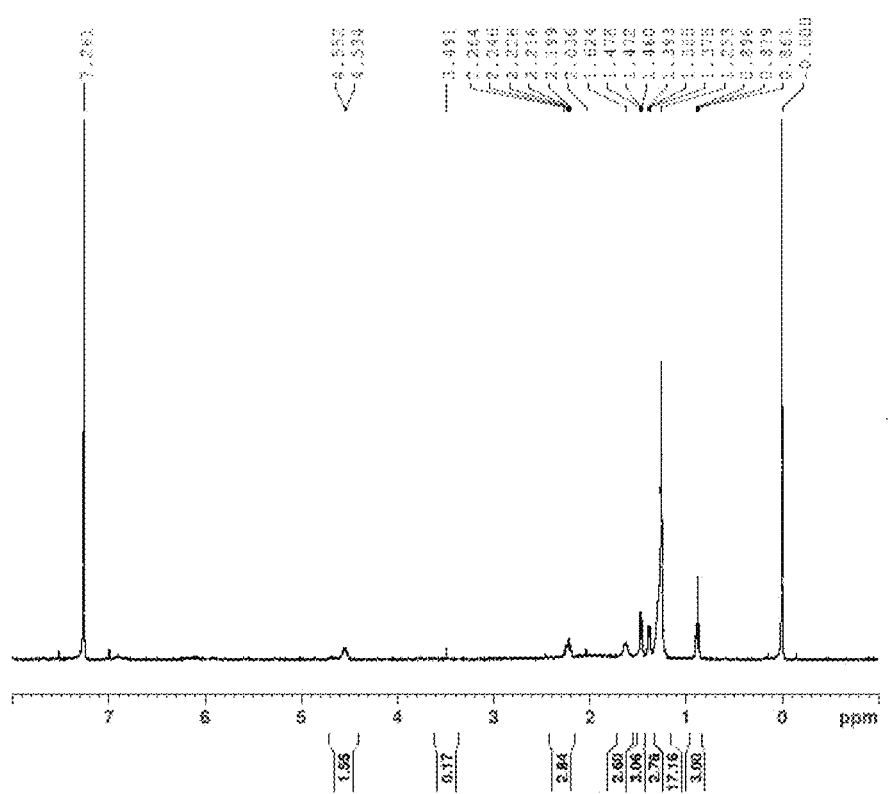
FIG. 3 shows an NMR spectrum of the self-assembled N-lauroyl-L-alanyl-L-alanine supramolecular polymer obtained according to the synthetic method in Example 1 in the present disclosure; where ppm is a unit representing one millionth chemical shift.

The mass of the resulting self-assembled N-lauroyl-L-alanyl-L-alanine polymer was 30.5 g; the yield was 89.3%; the content of lauric acid was not detectable; and the melting point was 148-150° C. FIG. 3 shows an NMR spectrum of the obtained N-lauroyl-L-alanyl-L-alanine. FIG. 7 shows a mass spectrum of the resulting N-lauroyl-L-alanyl-L-alanine.

It was found by experimentation that, if stirring was conducted at ambient pressure for the above reaction, a small amount of lauric acid could still be found by examining the reaction system. No self-assembled N-lauroyl-L-alanyl-L-alanine polymer could be obtained in the final product.

Embodiment 2

16.0 g (0.1 mol) L-alanyl-L-alanine and 6.0 g (0.15 mol) sodium hydroxide were dissolved in a mixed solution of 450 mL distilled water and 450 mL acetonitrile in a 2 L three-necked flask at ambient temperature, and stirred uniformly to obtain a sodium L-alanyl-L-alanine solution.

Under the condition of 25° C., 17.52 g (0.08 mol) lauroyl chloride was added dropwise slowly to the L-alanyl-L-alanine salt solution, and then a 30% sodium hydroxide solution was added dropwise to allow the reaction system to have a pH=9. After the addition was complete, stirring was continued for 0.5 h at 50° C. to obtain a pasty N-lauroyl-L-alanyl-L-alanine salt.

Hydrochloric acid was added to the pasty N-lauroyl-L-alanyl-L-alanine salt to acidify it to a pH=3-4. A white solid precipitated gradually. Then, the resultant was placed in an ice bath for 3 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:10:0.2:0.002. Stirring was conducted for 3 h at a temperature of 25° C. and a pressure of 50 kg, so that lauric acid in a small amount was completely consumed. Then, cooling and filtering were conducted. The resulting solid was washed twice with pure water, and finally dried at 70° C. to obtain a self-assembled N-lauroyl-L-alanyl-L-alanine polymer.

The mass of the resulting self-assembled N-lauroyl-L-alanyl-L-alanine polymer was 32.35 g; the yield was 94.72%; and the melting point was 148-150° C.

Embodiment 3

16.0 g (0.1 mol) L-alanyl-L-alanine and 4.0 g (0.1 mol) sodium hydroxide were dissolved in a mixed solution of 450 mL distilled water and 600 mL acetonitrile in a 2 L three-necked flask at ambient temperature, and stirred uniformly to obtain a sodium L-alanyl-L-alanine solution.

Under the condition of 25° C., 21.9 g (0.1 mol) lauroyl chloride was added dropwise slowly to the L-alanyl-L-alanine salt solution, and then a 80% sodium hydroxide solution was added dropwise to allow the reaction system to have a pH=9. After the addition was complete, stirring was continued for 3.5 h at 5° C. to obtain a pasty N-lauroyl-L-alanyl-L-alanine salt.

Hydrochloric acid was added to the pasty N-lauroyl-L-alanyl-L-alanine salt to acidify it to a pH=3-4. A white solid precipitated gradually. Then, the resultant was placed in an ice bath for 1 h. Filtering was conducted to obtain a crude N-lauroyl-L-alanyl-L-alanine product.

A mixed solvent of water and ethanol, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and ethanol, L-alanine, and p-toluenesulfonic acid were added at a molar ratio of 1:5:0.2:0.001. Stirring was conducted for 1 h at a temperature of 100° C. and a pressure of 5 kg, so that lauric acid in a small amount was completely consumed. Then, cooling and filtering were conducted. The resulting solid was washed twice with pure water, and finally dried at 130° C. to obtain a self-assembled N-lauroyl-L-alanyl-L-alanine polymer.

The mass of the resulting self-assembled N-lauroyl-L-alanyl-L-alanine polymer was 29.15 g; the yield was 85.35%; the content of lauric acid was not detectable; and the melting point was 148-150° C.

Embodiment 4

27.1 g (0.1 mol) N-lauroyl-L-alanine and 69.48 g (0.5 mol) thionyl chloride were mixed and reacted for 2 h in a 500 mL three-necked flask at room temperature. After the reaction was complete, the excess thionyl chloride was evaporated. After cooling, 100 mL pentan-2-one and 2 g activated carbon were added, and decolorization, filtration and reduced pressure distillation were preformed in sequence to take away the residual thionyl chloride. 100 mL anhydrous acetone was added to dissolve the acyl chloride in the N-lauroyl-L-alanine to obtain a solution of N-lauroyl-L-alanyl chloride in acetone.

8.9 g (0.1 mol) L-alanine and 4.0 g (0.1 mol) sodium hydroxide were dissolved in a mixed solution of 450 mL distilled water and 450 mL acetone in a 2 L three-necked flask at ambient temperature, and stirred uniformly to obtain a sodium L-alanine solution.

Under the condition of 25° C., 0.1 mol N-lauroyl-L-alanyl chloride in the acetone solution obtained above was added dropwise slowly to the L-alanine salt solution, and then a 50% sodium hydroxide solution was added dropwise to allow the reaction system to have a pH=9. After the addition was complete, stirring was continued for 2 h at 25° C. to obtain a pasty N-lauroyl-L-alanyl-L-alanine salt.

Hydrochloric acid was added to the pasty N-lauroyl-L-alanyl-L-alanine salt to acidify it to a pH=3-4. A white solid precipitated gradually. Then, the resultant was placed in an ice bath for 2 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:10:0.2:0.002. Stirring was conducted for 3 h at a temperature of 25° C. and a pressure of 50 kg, so that lauric acid in a small amount was completely consumed. Then, cooling and filtering were conducted. The resulting solid was washed twice with pure water, and finally dried at 70° C. to obtain a self-assembled N-lauroyl-L-alanyl-L-alanine polymer.

The mass of the resulting self-assembled N-lauroyl-L-alanyl-L-alanine polymer was 31.1 g; the yield was 90.7%; the content of lauric acid was not detectable; and the melting point was 148-150° C.

Embodiment 5

27.1 g (0.1 mol) N-lauroyl-L-alanine and 4.53 g (0.033 mol) phosphorus trichloride were added to a 250 mL three-necked flask at ambient temperature, and heated to 90° C. under the protection of nitrogen to react for 2-3 h. After the reaction was complete, the phosphorous acid was separated off, and the flask was cooled to room temperature. 100 mL anhydrous acetone was added to dissolve the acyl chloride in the N-lauroyl-L-alanine to obtain a solution of N-lauroyl-L-alanyl chloride in acetone.

8.9 g (0.1 mol) L-alanine and 4.0 g (0.1 mol) sodium hydroxide were dissolved in a mixed solution of 450 mL distilled water and 450 mL acetone in a 2 L three-necked flask at ambient temperature, and stirred uniformly to obtain a sodium L-alanine solution.

Under the condition of 25° C., 0.1 mol the solution of N-lauroyl-L-alanyl chloride in acetone obtained above was added dropwise slowly to the L-alanine salt solution, and then a 50% sodium hydroxide solution was added dropwise to allow the reaction system to have a pH=9. After the addition was complete, stirring was continued for 2 h at 25° C. to obtain a pasty N-lauroyl-L-alanyl-L-alanine salt.

Hydrochloric acid was added to the pasty N-lauroyl-L-alanyl-L-alanine salt to acidify it to a pH=3-4. A white solid precipitated gradually. Then, the resultant was placed in an ice bath for 2 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:10:0.2:0.002. Stirring was conducted for 3 h at a temperature of 25° C. and a pressure of 50 kg, so that lauric acid in a small amount was completely consumed. Then, cooling and filtering were conducted. The resulting solid was washed twice with pure water, and finally dried at 70° C. to obtain a self-assembled N-lauroyl-L-alanyl-L-alanine polymer.

The mass of the resulting self-assembled N-lauroyl-L-alanyl-L-alanine polymer was 31.6 g; the yield was 92.3%; the content of lauric acid was not detectable; and the melting point was 148-150° C.

Embodiment 6

40.65 g (0.15 mol) N-lauroyl-L-alanine and 69.48 g (0.5 mol) thionyl chloride were mixed and reacted for 3 h in a 1 L three-necked flask at ambient temperature. After the reaction was complete, the excess thionyl chloride was evaporated. After cooling, 120 mL pentan-2-one and 1 g activated carbon were added, and decolorization, filtration and reduced pressure distillation were performed in sequence to take away the residual thionyl chloride. Then, 80 mL anhydrous acetone was added to dissolve the acyl chloride in the N-lauroyl-L-alanine to obtain a solution of N-lauroyl-L-alanyl chloride in acetone.

8.9 g (0.1 mol) L-alanine and 4.0 g (0.1 mol) potassium hydroxide were dissolved in a mixed solution of 450 mL distilled water and 600 mL acetonitrile in a 2 L three-necked flask at ambient temperature, and stirred uniformly to obtain a sodium L-alanine solution.

Under the condition of 25° C., 0.1 mol N-lauroyl-L-alanyl chloride in the acetone solution obtained above was added dropwise slowly to the L-alanine salt solution, and then a 80% sodium hydroxide solution was added dropwise to allow the reaction system to have a pH=9. After the addition was complete, stirring was continued for 3.5 h at 5° C. to obtain a pasty N-lauroyl-L-alanyl-L-alanine salt.

Hydrochloric acid was added to the pasty N-lauroyl-L-alanyl-L-alanine salt to acidify it to a pH=3-4. A white solid precipitated gradually. Then, the resultant was placed in an ice bath for 1 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:10:0.2:0.002. Stirring was conducted for 3 h at a temperature of 25° C. and a pressure of 50 kg, so that lauric acid in a small amount was completely consumed. Then, cooling and filtering were conducted. The resulting solid was washed twice with pure water, and finally dried at 70° C. to obtain a self-assembled N-lauroyl-L-alanyl-L-alanine polymer.

The mass of the resulting self-assembled N-lauroyl-L-alanyl-L-alanine polymer was 29.95 g; the yield was 87.72%; the content of lauric acid was not detectable; and the melting point was 148-150° C.

Embodiment 7

27.1 g (0.1 mol) N-lauroyl-L-alanine and 9.9 g (0.033 mol) triphosgene ($C_3Cl_6O_3$) were dissolved in a mixed solution of 200 mL chloroform and 5 mL DMF (dimethylformamide) in a 1 L three-necked flask, and reacted under magnetic stirring at 40° C. for 6 hours. After the reaction was complete, the remaining chloroform was evaporated to obtain N-lauroyl-L-alanyl chloride.

13.95 g (0.1 mol) methyl L-alanine hydrochloride, 10.1 g (0.1 mol) triethylamine and 23.55 g (0.1 mol) N-lauroyl-L-alanyl chloride were dissolved in 500 mL acetone in a 1 L three-necked flask, reacted under magnetic stirring at 0° C. for 2 hours, and then heated to room temperature to continue the reaction under magnetic stirring for 5 hours. After the reaction was complete, the remaining acetone was evaporated to obtain methyl N-lauroyl-L-alanyl-L-alanine.

35.6 g (0.1 mol) methyl N-lauroyl-L-alanyl-L-alanine and 7.2 g (0.3 mol) lithium hydroxide were dissolved in a mixed solution of 500 mL methanol and 100 mL water in a 1 L three-necked flask, and reacted under magnetic stirring for 6 hours. After the reaction was complete, the methanol was evaporated to obtain a pasty N-lauroyl-L-alanyl-L-alanine salt.

10% hydrochloric acid was added to the pasty N-lauroyl-L-alanyl-L-alanine salt to acidify it to a pH=3-4. A white solid precipitated gradually. Then, the resultant was placed in an ice bath for 2 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:10:0.2:0.002. Stirring was conducted for 3 h at a temperature of 25° C. and a pressure of 50 kg, so that lauric acid in a small amount was completely consumed. Then, cooling and filtering were conducted. The resulting solid was washed twice with pure water, and finally dried at 70° C. to obtain a self-assembled N-lauroyl-L-alanyl-L-alanine polymer.

The mass of the resulting self-assembled N-lauroyl-L-alanyl-L-alanine polymer was 31.9 g; the yield was 93.4%; the content of lauric acid was not detectable; and the melting point was 148-150° C.

Embodiment 8

40.65 g (0.15 mol) N-lauroyl-L-alanine and 9.9 g (0.033 mol) triphosgene ($C_3Cl_6O_3$) were dissolved in a mixed solution of 400 mL chloroform and 1 mL pyridine in a 1 L three-necked flask, and reacted under magnetic stirring at 50° C. for 4 hours. After the reaction was complete, the remaining chloroform was evaporated to obtain N-lauroyl-L-alanyl chloride.

11.16 g (0.08 mol) methyl L-alanine hydrochloride, 7.91 g (0.1 mol) pyridine and 23.55 g (0.1 mol) N-lauroyl-L-alanyl chloride were dissolved in 700 mL acetone in a 1 L three-necked flask, reacted under magnetic stirring at 5° C. for 3 hours, and then heated to room temperature to continue the reaction under magnetic stirring for 4 hours. After the reaction was complete, the remaining acetone was evaporated to obtain methyl N-lauroyl-L-alanyl-L-alanine.

35.6 g (0.1 mol) methyl N-lauroyl-L-alanyl-L-alanine and 5.6 g (0.1 mol) potassium hydroxide were dissolved in a mixed solution of 300 mL ethanol and 100 mL water in a 1 L three-necked flask, and reacted under magnetic stirring for 4 hours. After the reaction was complete, the methanol was evaporated to obtain a pasty N-lauroyl-L-alanyl-L-alanine salt.

15% hydrochloric acid was added to the pasty N-lauroyl-L-alanyl-L-alanine salt to acidify it to a pH=3-4. A white solid precipitated gradually. Then, the resultant was placed in an ice bath for 1 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:10:0.2:0.002. Stirring was conducted for 3 h at a temperature of 25° C. and a pressure of 50 kg, so that lauric acid in a small amount was completely consumed. Then, cooling and filtering were conducted. The resulting solid was washed twice with pure water, and finally dried at 70° C. to obtain a self-assembled N-lauroyl-L-alanyl-L-alanine polymer.

The mass of the resulting self-assembled N-lauroyl-L-alanyl-L-alanine polymer was 32.4 g; the yield was 94.9%; the content of lauric acid was not detectable; and the melting point was 148-150° C.

Embodiment 9

27.1 g (0.15 mol) N-lauroyl-L-alanine and 9.9 g (0.033 mol) triphosgene ($C_3Cl_6O_3$) were dissolved in a mixed solution of 700 mL chloroform and 10 mL 1-methylpiperidine in a 1 L three-necked flask, and reacted under magnetic stirring at 30° C. for 8 hours. After the reaction was complete, the remaining chloroform was evaporated to obtain N-lauroyl-L-alanyl chloride.

11.16 g (0.08 mol) methyl L-alanine hydrochloride, 8.1 g (0.08 mol) triethylamine and 23.55 g (0.1 mol) N-lauroyl-L-alanyl chloride were dissolved in 300 mL acetone in a 1 L three-necked flask, reacted under magnetic stirring at 3° C. for 7 hours, and then heated to room temperature to continue the reaction under magnetic stirring for 6 hours. After the reaction was complete, the remaining acetone was evaporated to obtain methyl N-lauroyl-L-alanyl-L-alanine.

35.6 g (0.1 mol) methyl N-lauroyl-L-alanyl-L-alanine and 20 g (0.5 mol) sodium hydroxide were dissolved in a mixed solution of 700 mL ethanol and 100 mL water in a 1 L three-necked flask, and reacted under magnetic stirring for 8 hours. After the reaction was complete, the methanol was evaporated to obtain a pasty N-lauroyl-L-alanyl-L-alanine salt.

5% hydrochloric acid was added to the pasty N-lauroyl-L-alanyl-L-alanine salt to acidify it to a pH=3-4. A white solid precipitated gradually. Then, the resultant was placed in an ice bath for 3 h. Filtering was conducted to obtain a crude N-lauroyl-L-alanyl-L-alanine product.

A mixed solvent of water and acetone, L-alanyl-L-alanine and p-toluenesulfonic acid were added to the crude N-lauroyl-L-alanyl-L-alanine product, wherein the crude N-lauroyl-L-alanyl-L-alanine product, the mixed solvent of water and acetone, L-alanine, and p-toluenesulfonic acid were added at a molar ratio of 1:10:0.2:0.002. Stirring was conducted for 3 h at a temperature of 25° C. and a pressure of 50 kg, so that lauric acid in a small amount was completely consumed. Then, cooling and filtering were conducted. The resulting solid was washed twice with pure water, and finally dried at 70° C. to obtain a self-assembled N-lauroyl-L-alanyl-L-alanine polymer.

The mass of the resulting self-assembled N-lauroyl-L-alanyl-L-alanine polymer was 30.9 g; the yield was 90.5%; the content of lauric acid was not detectable; and the melting point was 148-150° C.

Figure 4A:
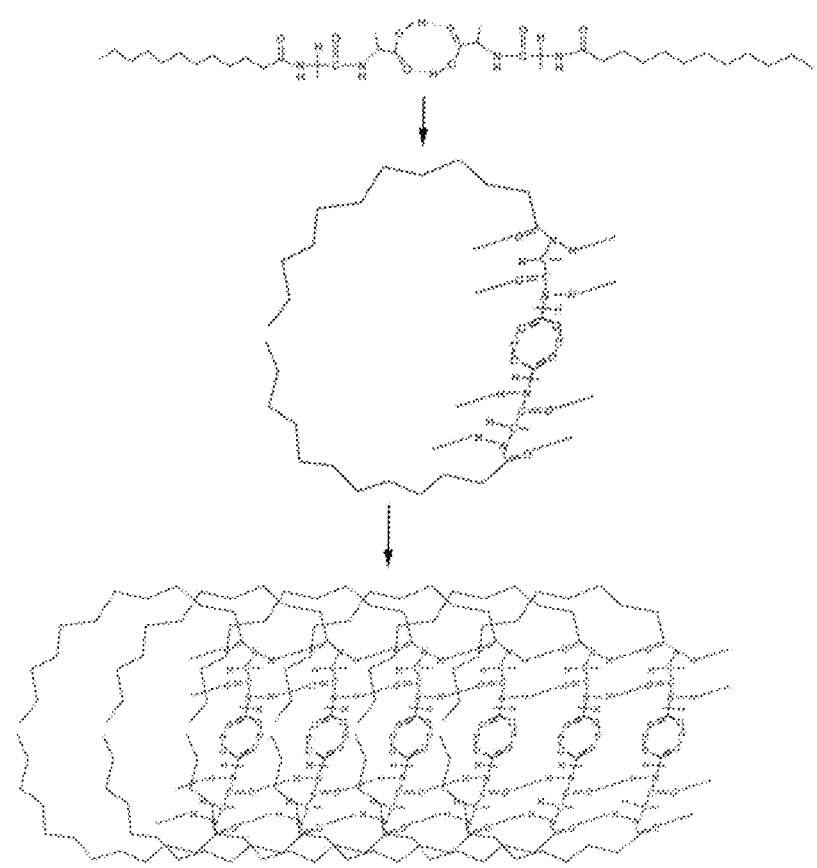
FIG. 4a is a diagram demonstrating formation of the structure of a supramolecular amino acid from the N-lauroyl-L-alanyl-L-alanine monomer obtained according to the synthetic method in Example 1 in the present disclosure.
Figure 4B:
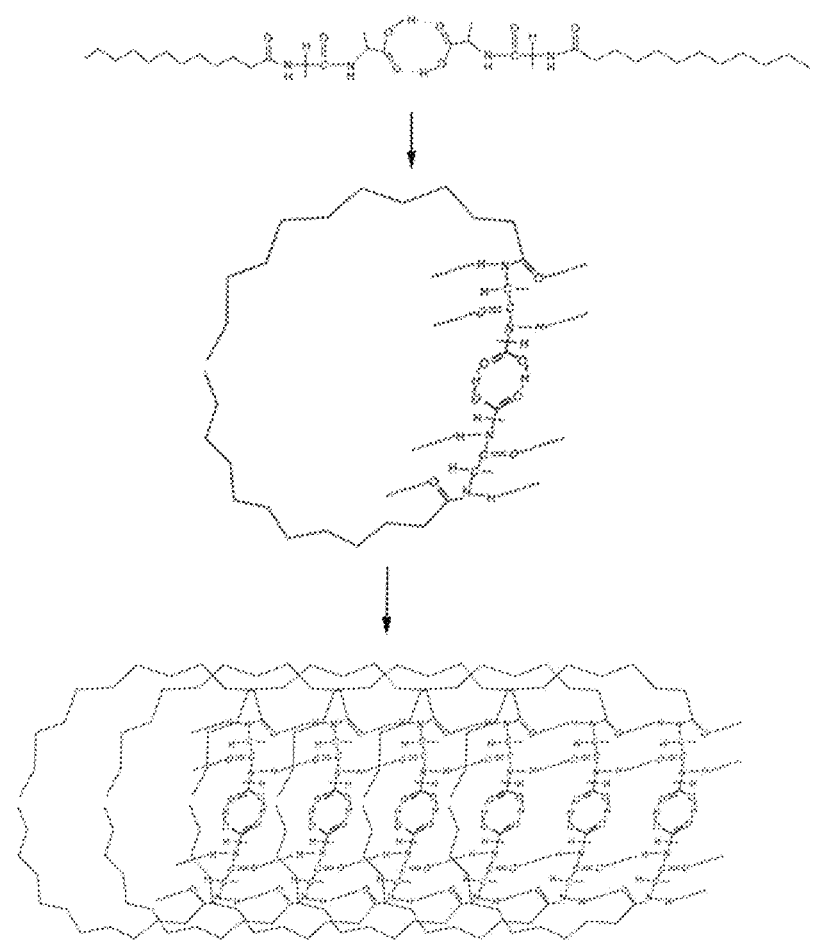
FIG. 4b is a diagram demonstrating formation of the structure of a supramolecular amino acid from the N-lauroyl-L-alanyl-L-alanine monomer obtained according to the synthetic method in Example 1 in the present disclosure.

Example 2 Structural Features of Self-Assembled N-Lauroyl-L-Alanyl-L-Alanine Polymer FIG. 4a is a diagram demonstrating formation of the structure of a supramolecular amino acid from the N-lauroyl-L-alanyl-L-alanine monomer in the self-assembled supramolecular amino acid polymer obtained according to the synthetic method in Example 1 in the present disclosure; and FIG. 4b is a diagram demonstrating formation of the structure of a supramolecular amino acid from the N-lauroyl-L-alanyl-L-alanine monomer obtained according to the synthetic method in Example 1 in the present disclosure. As can be seen from the above NMR spectrum and mass spectrum, the N-lauroyl-L-alanyl-L-alanine produced by the inventive process is substantially free of lauric acid impurity. The N-lauroyl-L-alanyl-L-alanine synthesized in this process can form three groups of hydrogen bonds, and there is an alkane structure of an eleven-carbon chain at each of both ends. According to the principle of oil-oil compatibility, the two lipophilic ends are coupled like a chain, connected end to end to form a ring. Also by means of hydrogen bonds and oil-oil compatibility, countless rings stack to form a columnar molecular cluster. Countless columnar molecular clusters further stack to form a special spatial structure—referred to as a supramolecular amino acid.

Figure 5A:
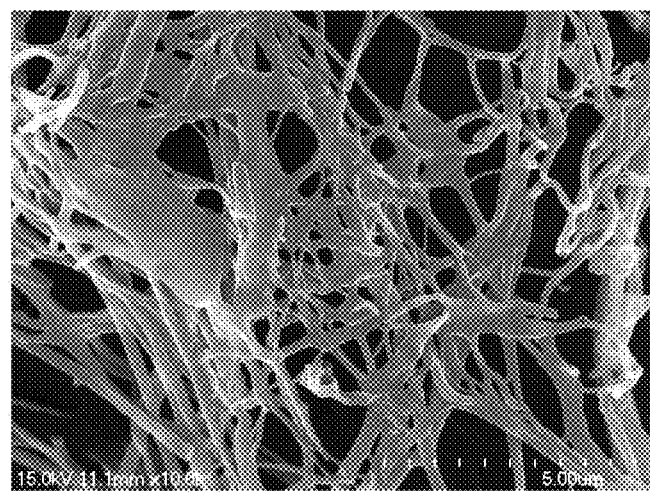
FIG. 5a shows a 10000× electron micrograph of the N-lauroyl-L-alanyl-L-alanine obtained according to the synthetic method in Example 1 in the present disclosure.
Figure 5B:
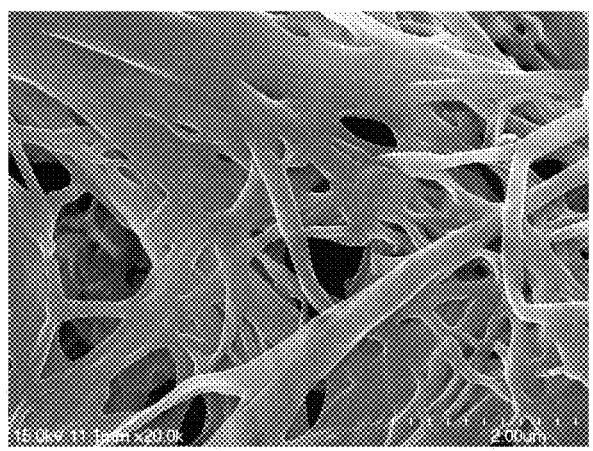
FIG. 5b shows a 20000× electron micrograph of the N-lauroyl-L-alanyl-L-alanine obtained according to the synthetic method in Example 1 in the present disclosure.
Figure 5C:
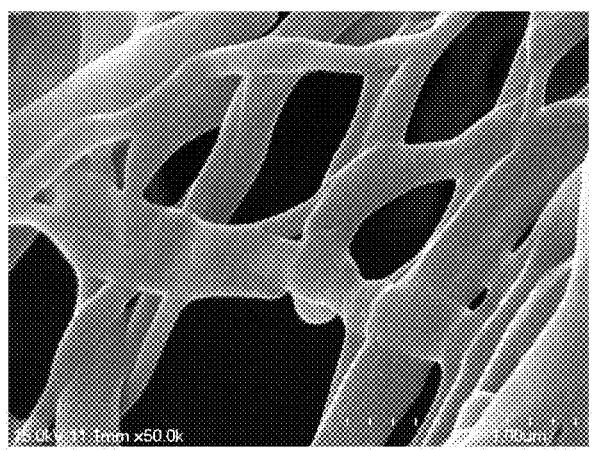
FIG. 5c shows a 50000× electron micrograph of the N-lauroyl-L-alanyl-L-alanine obtained according to the synthetic method in Example 1 in the present disclosure.

Countless columnar molecular clusters further stack to form a special spatial structure. Due to the existence of two or more configurations, there will be a certain angular deviation when they are stacked, and branches will be formed when they are stacked. FIGS. 5a, 5b and 5c show the 10000×, 20000× and 50000× electron micrographs of the self-assembled N-lauroyl-L-alanyl-L-alanine polymer obtained according to the synthetic method in Example 1 in the present disclosure respectively. FIGS. 5a, 5b and 5c prove in a better way the principle by which the N-lauroyl-L-alanyl-L-alanine monomer forms the supramolecular amino acid, and the structure thereof.

Figure 6:
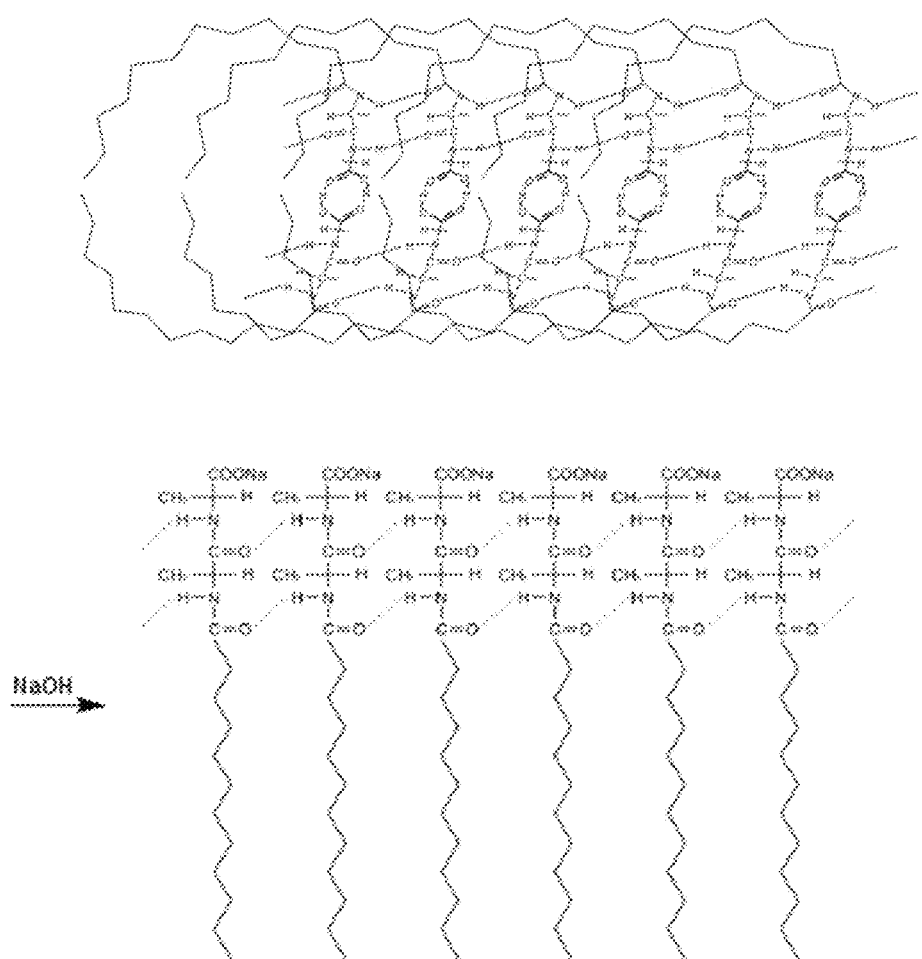
FIG. 6 is a diagram demonstrating further formation of a sodium salt from the supramolecular amino acid formed from the N-lauroyl-L-alanyl-L-alanine obtained according to the synthetic method in Example 1 in the present disclosure.

After the supramolecular amino acid was formed, the supramolecular amino acid further reacted with sodium hydroxide to form a sodium salt structure of the supramolecular amino acid, as shown by FIG. 6. As shown by FIG. 6, the sodium salt structure is hydrophilic at one side and oleophilic at the other side. The molecules are linked by hydrogen bonds to form a special two-dimensional network structure having a regular arrangement. Since the carbon chain length is similar to that of stearic acid, the sodium salt has a strong ability to combine with oil, and can be used as a primary surfactant.

The presence of lauric acid prevents formation of infinite hydrogen bond linkages between N-lauroyl-L-alanyl-L-alanine molecules. Experimental data have verified that N-lauroyl-L-alanyl-L-alanine containing lauric acid impurity cannot provide the above electron micrographs. The inventive process solves the problem of residual lauric acid impurity, such that hydrogen bonds can form easily between N-lauroyl-L-alanyl-L-alanine molecules which are thus linked infinitely, and special properties are provided. The inventive process effectively solves the problem that the residual lauric acid impurity damages the N-lauroyl-L-alanyl-L-alanine structure, and further affects or damages the properties of N-lauroyl-L-alanyl-L-alanine. As a result, hydrogen bonds can form easily between N-lauroyl-L-alanyl-L-alanine molecules which are thus linked infinitely, and special properties are provided.

In further experiments herein, N-decanoyl-L-alanyl-L-alanine was used to conduct structural studies under the same conditions, but the aforementioned three-dimensional network structure was not found. The reason may be that the carbon chain of N-decanoyl-L-alanyl-L-alanine is short, and the lipophilic ends of two molecules cannot form a ring. It can thus be inferred that the carbon chain of the lipophilic group should have 12-18 carbons, and the fatty acyl-L-alanyl-L-alanine formed from such a carbon chain with L-alanyl-L-alanine can also form the aforementioned spatial structure by way of intermolecular hydrogen bonding and oil-oil compatibility with fatty acid being removed. Once this structure is formed, it is very stable. Experiments prove that the addition of less than 10% fatty acid will not damage the stability and properties of the existing structure, and thus will not affect its applications.

Example 3 Applications of Self-Assembled N-Lauroyl-L-Alanyl-L-Alanine Polymer

Application Embodiment 1 Evaluation of Inhibitory Effect of Self-Assembled N-Lauroyl-L-Alanyl-L-Alanine Polymer on Bacteria 10 g of the self-assembled N-lauroyl-L-alanyl-L-alanine polymer synthesized according to the method in Embodiment 1 was added to water, and neutralized to pH=6-7 by adding a 10% aqueous sodium hydroxide solution, thereby formulating a 100 mL aqueous solution. 5 mL of the stock solution was used separately to soak fruit plates pre-inoculated with common bacteria such as *Staphylococcus aureus, Escherichia coli, Pseudomonas aeruginosa, Candida albicans, Pseudomonas aeruginosa*, etc, respectively. After a certain period of time of action, the plates were rinsed once with clean water, and then residual bacteria on the fruit plates were determined. The test results are shown in Table 1:

TABLE 1

Analysis on the antibacterial effect of the self-assembled N-lauroyl-L-alanyl-L-alanine polymer

| No. | Test items | Unit | Technical requirement | Test result | Individual evaluation |
|---|---|---|---|---|---|
| 1 | Bacteriostasis rate for *Escherichia coli* (8099), % (action for 2 minutes) | — | — | 100 | — |
| 2 | Bacteriostasis rate for *Staphylococcus aureus* (ATCC 6538), % (action for 2 minutes) | — | — | 100 | — |

TABLE 1-continued

Analysis on the antibacterial effect of the self-assembled N-lauroyl-L-alanyl-L-alanine polymer

| No. | Test items | Unit | Technical requirement | Test result | Individual evaluation |
|---|---|---|---|---|---|
| 3 | Bacteriostasis rate for *Staphylococcus aureus* (ATCC 6538), % (action for 3 minutes) | — | — | 100 | — |
| 4 | Bacteriostasis rate for *Candida albicans* (ATCC 10231), % (action for 3 minutes) | — | — | 100 | — |
| 5 | Bacteriostasis rate for *Pseudomonas aeruginosa*, % (action for 3 minutes) | — | — | 100 | — |
| 6 | Total number of bacteria | CFU/mL | ≤1000 | <10 | Qualified |
| 7 | Number of coliforms | MPN/100 mL | ≤3 | <3 | Qualified |

As can be seen from the above data, the self-assembled N-lauroyl-L-alanyl-L-alanine polymer solution synthesized according to the inventive method had a significant inhibitory effect on *Escherichia coli, Staphylococcus aureus* and *Candida albicans*. After the stock solution, i.e. the self-assembled N-lauroyl-L-alanyl-L-alanine polymer solution, was applied to *Escherichia coli* for 2 minutes, the bacteriostasis rate reached 100%. After the stock solution was applied to *Staphylococcus aureus* for 2 minutes, the bacteriostasis rate reached 100%. The bacteriostasis rate also reached 100% when the stock solution acted on *Candida albicans* for 3 minutes. After the stock solution was applied to *Pseudomonas aeruginosa* for 2 minutes, the bacteriostasis rate also reached 100%.

Comparative Embodiment 1 Evaluation of Inhibitory Effect of Self-Assembled N-Lauroyl-L-Alanine Polymer on Bacteria The antibacterial effect of a self-assembled N-lauroyl-L-alanine polymer was tested under the same conditions, as shown in Table 2 below.

Comparative Embodiment 1 only differs from Embodiment 1 in substitute of the self-assembled N-lauroyl-L-alanine polymer for the self-assembled N-lauroyl-L-alanyl-L-alanine polymer, with the other conditions being the same as in Embodiment 1.

TABLE 2

Inhibitory effect of self-assembled N-lauroyl-L-alanine polymer on bacteria

| No. | Test items | Unit | Technical requirement | Test result | Individual evaluation |
|---|---|---|---|---|---|
| 1 | Bacteriostasis rate for *Escherichia coli* (8099), % (action for 2 minutes) | — | — | 96.3 | — |
| 2 | Bacteriostasis rate for *Escherichia coli* (8099), % (action for 5 minutes) | — | — | 100 | — |
| 3 | Bacteriostasis rate for *Staphylococcus aureus* (ATCC 6538), % (action for 2 minutes) | — | — | 100 | — |
| 4 | Bacteriostasis rate for *Staphylococcus aureus* (ATCC 6538), % (action for 5 minutes) | — | — | 100 | — |
| 5 | Bacteriostasis rate for *Candida albicans* (ATCC 10231), % (action for 5 minutes) | — | — | 100 | — |
| 6 | Total number of bacteria | CFU/mL | ≤1000 | <10 | Qualified |
| 7 | Number of coliforms | MPN/100 mL | ≤3 | <3 | Qualified |

By comparing Table 1 and Table 2, it can be seen that the inventive self-assembled N-lauroyl-L-alanyl-L-alanine polymer has an apparently better antibacterial effect than that of the self-assembled N-lauroyl-L-alanine polymer. As illustrated by the above data, the inventive self-assembled N-lauroyl-L-alanyl-L-alanine polymer has an unexpected inhibitory effect on bacteria.

As known from the common knowledge in the art, the size of bacteria is usually 0.5-5 μm. The gap between the columnar clusters of the supramolecular structure formed from the inventive N-lauroyl-L-alanyl-L-alanine free of lauric acid is also micron sized, so bacteria can be entrapped and removed. Hence, it can be said that nano-sized foam micropores can be produced.

Embodiment 2 Evaluation of Pesticide Removing Effect of Self-Assembled N-Lauroyl-L-Alanyl-L-Alanyl-L-Alanine Polymer 100 g of a green vegetable (*Brassica chinensis* L.) in two portions were sprayed with pesticides (methamidophos and acephate) in advance. One portion was directly soaked in 1 L clean water, and then taken out for detection of residual pesticide on the vegetable leaves. The result is designated as "pre-rinse". The other portion was rinsed with a solution formulated using the self-assembled N-lauroyl-L-alanyl-L-alanine polymer synthesized according to the method in Example 3. The measurement result is designated as "post-rinse". The operation is described as follows:

10 g of the self-assembled N-lauroyl-L-alanyl-L-alanine polymer synthesized according to the method in Example 1 was added to water, and neutralized to pH=6-7 by adding a 10% aqueous sodium hydroxide solution, thereby formulating a 100 mL aqueous solution. The other portion of the 100 g green vegetable (*Brassica chinensis* L.) sprayed with the pesticides (methamidophos and acephate) in advance was cut into small pieces, soaked in 5 mL of the stock solution for 2 minutes, taken out, flushed with 500 mL clean water, and then taken out for detecting residual pesticide on the vegetable leaves. Table 3 shows data comparing residual pesticides before and after the rinsing:

TABLE 3

Analysis on pesticide removing effect of self-assembled N-lauroyl-L-alanyl-L-alanine polymer

| No. | Test items | Pre-rinsing mg/kg | Post-rinsing mg/kg | Removal rate % |
|---|---|---|---|---|
| 1 | methamidophos | 17.26 | 1.51 | 90.6 |
| 2 | acephate | 39.53 | 2.67 | 93.2 |

As can be seen from the above data, the self-assembled N-lauroyl-L-alanyl-L-alanine polymer solution, a surface active substance used in the present disclosure, has a significant effect in removing methamidophos and acephate. After the action for 2 minutes, the removal rate of methamidophos reached 90.6%; and the removal rate of acephate reached 93.2%. The effect is obvious.

Comparative Embodiment 2 Evaluation of Pesticide Removing Effect of Self-Assembled N-Lauroyl-L-Alanine Polymer The antibacterial effect of a self-assembled N-lauroyl-L-alanine polymer was tested under the same conditions, as shown in Table 4 below.

Comparative Embodiment 2 only differs from Embodiment 2 in substitute of the self-assembled N-lauroyl-L-alanine polymer for the self-assembled N-lauroyl-L-alanyl-L-alanine polymer, with the other conditions being the same as in Embodiment 2.

TABLE 4

Analysis on pesticide removing effect of self-assembled N-lauroyl-L-alanine polymer

| No. | Test items | Pre-rinsing mg/kg | Post-rinsing mg/kg | Removal rate % |
|---|---|---|---|---|
| 1 | methamidophos | 16.06 | 5.68 | 64.63 |
| 2 | acephate | 38.48 | 9.75 | 74.66 |

By comparing Table 3 and Table 4, it can be seen that the inventive self-assembled N-lauroyl-L-alanyl-L-alanine polymer has an apparently better pesticide removing effect than that of the self-assembled N-lauroyl-L-alanine polymer.

As can be seen from the above description, the inventive preparation method of the self-assembled N-lauroyl-L-alanyl-L-alanine supramolecular polymer has simple process steps and mild reaction conditions, and is thus suitable for industrial production. The self-assembled N-lauroyl-L-alanyl-L-alanine polymer prepared by the inventive method has a high purity, and the lauric acid content is undetectable by HPLC. Hence, the influence of lauric acid on product quality is effectively avoided. The resulting N-lauroyl-L-alanyl-L-alanine is stable in structure and properties. It has sound bacteriostasis rates, wherein the bacteriostasis rates for *Escherichia coli*, *Staphylococcus aureus*, *Candida albicans* and *Pseudomonas aeruginosa* can all reach 100%. It can remove residual pesticide effectively, wherein the removal rate of methamidophos can reach 90.6%, and the removal rate of acephate can reach 93.2%. At the same time, it has good deodoring ability. It is promising for use in the daily chemical industry, agriculture, and pharmaceutical industry.

Examples 4-8

In these examples, the total weight parts of the amino acid toothpaste body are 100. The ingredients and specific contents thereof in the toothpastes are shown in Table 5:

TABLE 5

Ingredients and contents in the toothpastes

| Starting materials | Amounts of starting materials | | | | |
|---|---|---|---|---|---|
| | Example 4 | Example 5 | Example 6 | Example 7 | Example 8 |
| Self-assembled N-lauroyl-L-alanyl-L-alanine polymer | 4.4 | 3 | 2 | 5 | 13.75 |

TABLE 5-continued

Ingredients and contents in the toothpastes

| Starting materials | Amounts of starting materials | | | | |
|---|---|---|---|---|---|
| | Example 4 | Example 5 | Example 6 | Example 7 | Example 8 |
| Carboxymethylcellulose | 4 | 6 | 4 | 6 | 3 |
| Hydrated silica | 35 | 35 | 33.4 | 35 | 33 |
| Water | 10 | 10 | 10 | 10 | 8 |
| Sorbitol | 37.5 | 35.5 | 35.5 | 33.5 | 32 |
| Glycerol | 5 | 6 | 6 | 6 | 5 |
| Polyglycol-400 | 2 | 2 | 2 | 2 | 3 |
| Edible essence | 1 | 1.5 | 1 | 1.5 | 1 |
| Chondrus Crispus carrageenan extract | 0.2 | 0.1 | 0.2 | 0.1 | 0.2 |
| Sodium saccharin | 0.2 | 0.2 | 0.2 | 0.2 | 0.2 |
| Sodium benzoate | 0.4 | 0.4 | 0.4 | 0.4 | 0.4 |
| Licorice extract | 0.1 | 0.1 | 0.1 | 0.1 | 0.15 |
| Purslane extract | 0.1 | 0.1 | 0.1 | 0.1 | 0.15 |
| CI42090 (brilliant blue aluminum lake) | 0.1 | 0.1 | 0.1 | 0.1 | 0.15 |

Examples 9-13

In these examples, the total weight parts of the amino acid toothpaste body are 100. The ingredients and specific contents thereof in the toothpastes are shown in Table 6:

TABLE 6

Ingredients and contents in the toothpastes

| Starting materials | Amounts of starting materials | | | | |
|---|---|---|---|---|---|
| | Example 9 | Example 10 | Example 11 | Example 12 | Example 13 |
| Self-assembled N-lauroyl-L-alanyl-L-alanine polymer | 25 | 6 | 10 | 0.1 | 1 |
| Carboxymethylcellulose | 3 | 6 | 4 | 6 | 5 |
| Hydrated silica | 32 | 35 | 33.4 | 41.3 | 42 |
| Water | 5 | 10 | 10 | 10 | 9 |
| Sorbitol | 25.2 | 32.5 | 32.5 | 32.1 | 32.75 |
| Glycerol | 5 | 6 | 6 | 6 | 5 |
| Polyglycol-400 | 2 | 2 | 2 | 2 | 3 |
| Edible essence | 1.5 | 1.5 | 1 | 1.5 | 1 |
| Chondrus Crispus carrageenan extract | 0.2 | 0.1 | 0.2 | 0.1 | 0.2 |
| Sodium saccharin | 0.3 | 0.2 | 0.2 | 0.2 | 0.2 |
| Sodium benzoate | 0.4 | 0.4 | 0.4 | 0.4 | 0.4 |
| Licorice extract | 0.1 | 0.1 | 0.1 | 0.1 | 0.15 |
| Purslane extract | 0.15 | 0.1 | 0.1 | 0.1 | 0.15 |
| CI42090 (brilliant blue aluminum lake) | 0.15 | 0.1 | 0.1 | 0.1 | 0.15 |

The toothpaste according to the formula of Example 4 was prepared with the following specific steps: formulating an aqueous solution with 10 g water, 37.5 g sorbitol, 0.2 g sodium saccharin, 2 g polyethylene glycol-400, 5 g glycerol, 0.4 g sodium benzoate, and placing the aqueous solution in a paste making machine. Then, 4 g carboxymethyl cellulose, 35 g hydrated silica, 0.2 g *Chondrus crispus* carrageenan extract, 0.1 g licorice extract and 0.1 g purslane extract were mixed, added to the paste making machine, stirred and ground for 20-30 minutes until the paste was uniform. Then, vacuum defoaming was performed. 4.4 g sodium N-lauroyl-L-alanyl-L-alanine polymer, 1 g edible essence (mint flavor), and 0.1 g CI42090 were added in sequence to the paste making machine, stirred and ground for 10-15 minutes until the paste was uniform. Then, defoaming was performed to obtain the amino acid toothpaste.

Examples 5-13 were all prepared using the method described in Example 4, which will not be repeated here.

According to the amounts in the formulae in Examples 4-13, amino acid toothpaste samples were prepared with different parts by weight of the amino acid surfactant by repeating the formulation tests several times. 100 volunteers with frequent toothache and gum bleeding were recruited to evaluate the effect. The frequency of use was once in the morning and once in the evening each day, the dosage was about 1 g paste per time, and the time for each brushing was about 5 minutes. As shown by the results, the toothpaste containing the amino acid surface active ingredient has obvious effects of analgesia, antiphlogosis and preventing gum bleeding. When evaluated from the two aspects of taste and deodorization, the weight percentage of the amino acid surface active ingredient in the toothpaste body is desirably 0.1-25%, preferably 0.5-10%, and most preferably 1-5%. When the amino acid surface active ingredient accounts for 1-5% by weight of the medicated toothpaste body, the pharmaceutical effect and taste of the toothpaste are in the best balance, and the removal of oral odor reaches the best level. At the same time, even if fruit is eaten immediately after teeth brushing, the taste of the fruit is not affected, and there is no feel of bitterness or aningeresting.

Example 14 Use of Self-Assembled N-Lauroyl-L-Alanyl-L-Alanine Polymer for Skin Care

TABLE 7

Starting materials and weight percentages thereof for skin care compositions

| Starting materials | Formula 1 | Formula 2 | Formula 3 | Formula 4 | Formula 5 | Formula 6 | Formula 7 |
|---|---|---|---|---|---|---|---|
| Natural oil mixture* | 57 | 80 | 64.3 | 64 | 65 | 51 | 57 |
| Corn starch | 40 | 15 | 25 | 25 | 0 | 25 | 40 |
| KTZ classical white mica | 0 | 0 | 0.5 | 0 | 0 | 0 | 0 |
| Titanium dioxide | 0 | 0 | 0.2 | 0 | 0 | 0 | 0 |
| Micronized titanium dioxide | 0 | 0 | 0 | 6 | 0 | 0 | 0 |
| Boron nitride (CaressnBN02 ex. Kobo) | 0 | 0 | 0 | 0 | 5 | 0 | 0 |
| Glycerol | 0 | 0 | 0 | 0 | 25 | 10 | 0 |
| Monolauroyl glyceride | 0 | 0 | 0 | 0 | 0 | 4 | 0 |
| Mss-500/20 | 0 | 0 | 0 | 0 | 0 | 0 | 0 |
| Self-assembled N-lauroyl-L-alanyl-L-alanine polymer | 3 | 5 | 10 | 5 | 5 | 10 | 0 |
| Lauroyl alanine (containing 2% or more lauric acid) | 0 | 0 | 0 | 0 | 0 | 0 | 3 |

*The natural oil mixture contains 40% grape seed oil, 37.2% sunflower seed oil and 22.8% aloe oil.

The specific steps for preparing Formula 1 shown in Table 7 include: adding 57% of the natural oil mixture and 40% of the corn starch into a mixer and homogenizing to disperse the particles first. The particles in the oil dispersion were then heated to 83-86° C. while mixing. 3% of the self-assembled N-lauroyl-L-alanyl-L-alanine polymer was added to the mixer while heating. The sample was heated and kept at 73-86° C. for 5-10 min. It was then cooled to a temperature between 65-72° C. while remaining mixable. The sample was then poured into a 30 ml tank to obtain the skin care composition, which was stored and used for evaluation. The skin care compositions of Formulae 2-6 were prepared using the same method as that for Formula 1, which will not be repeated here.

In the skin care compositions obtained according to the above examples, different types and amounts of particulate substances were added to the raw materials. As shown by the results, the addition of particulate substances increased the viscosity of the oil. In addition, the self-assembled N-lauroyl-L-alanyl-L-alanine polymer helped to stably suspend the solid organic/inorganic particles or an oil-miscible liquid such as glycerol in the thickened natural oils to provide additional benefits to skin.

Four kinds of oil-insoluble particles, such as starch, $TiO_2$, mica, boron nitride particles (Caress BN02 from Kobo) and an oil-miscible liquid such as glycerol were used. The same natural oil mixture, comprising 40% grape seed oil, 37.2% sunflower seed oil and 22.8% aloe oil, was used in Formulae 1-6. As shown by the results, the compositions obtained from all the formulae shown in Table 3 were stable at room temperature and in an oven at 48° C. with no separation of particles. In Formula 7 for comparison, lauroyl alanine (containing at least 2% lauric acid) was used instead of the self-assembled N-lauroyl-L-alanyl-L-alanine polymer used in Formula 1. As a result, it was found that the resulting composition was unstable after 48 hours in an oven at 48° C., and oil emerged.

Example 15 Application Example of Supramolecular Amino Acids in Laundry Liquid

TABLE 8

Amino acid laundry liquid

| | Weight percentages of components | |
|---|---|---|
| Components | Formula 1 | Formula 2 |
| Water | 78 | 78 |
| Self-assembled N-lauroyl-L-alanyl-L-alanine polymer | 10 | 0 |
| Sodium hydroxide | 1.4 | 1.4 |
| Lauroyl alanine (containing 2% lauric acid) | 0 | 10 |
| Decyl glucoside | 5 | 5 |
| Cocamidopropyl betaine | 5 | 5 |
| GPL | 0.5 | 0.5 |
| DMDM | 0.1 | 0.1 |
| Fragrance | 0.05 | 0.05 |

The laundry liquid formulated in accordance with Formula 1 in Table 8 was tested by Suzhou Institute of Product Quality Supervision and Inspection, and the detergent power was higher than or equal to the detergent power of the standard laundry liquid. The resulting samples had a higher detergent power on JB01, JB02, and JB03 dirty cloth than the detergent power of the standard laundry liquid on JB01, JB02, JB03 dirty cloth. As tested by Suzhou Institute of Product Quality Supervision and Inspection, the laundry liquid formulated according to Formula 2 had a detergent power lower than that of the standard laundry liquid.

Example 16 Application Example of Surfactant Comprising Supramolecular Amino Acid and Self-Assembled Polymer Formed from N-Lauroyl-L-Alanine in Facial Cleanser

TABLE 9

Supramolecular amino acid facial cleanser

| Components | Percentages of starting materials in the formula |
|---|---|
| Water | 82 |
| Self-assembled N-lauroyl-L-alanine polymer | 1 |
| Self-assembled N-lauroyl-L-alanyl-L-alanine polymer | 3 |
| Sodium hydroxide | |
| Cocamidopropyl betaine | 7.8 |
| Glycerol | 4.5 |
| Glutamic acid N,N-diacetate tetrasodium salt | 0.3 |
| GPL | 0.5 |
| DMDM | 0.1 |
| Fragrance | 0.05 |

Salts formed from the self-assembled N-lauroyl-L-alanyl-L-alanine polymer and the self-assembled N-lauroyl-L-alanine polymer in alkaline aqueous systems are clean surfactants. They are mild, non-irritating, good at oil control, and more suitable for sensitive skin.

In addition, as can be understood by those skilled in the art, although some embodiments described herein include certain features included in other embodiments but not other features, combinations of features in different embodiments are intended to be included in the scope of the present disclosure, and form different embodiments. For example, in the following claims, any one of the claimed embodiments can be used in any combination.

What is claimed is:

1. A self-assembled amino acid supramolecular polymer or a salt thereof, wherein the polymer is formed by hydrogen bonding N-lauroyl-L-alanyl-L-alanine monomers, wherein the salt thereof is formed by hydrogen bonding salt N-lauroyl-L-alanyl-L-alanine monomers, wherein the polymer or the salt thereof contains less than 0.02 wt. % lauric acid based on a total weight of the polymer or the salt thereof, and wherein the polymer or the salt thereof has a melting point of 148-150° C.

2. The self-assembled amino acid supramolecular polymer or the salt thereof according to claim 1, wherein said hydrogen bonding N-lauroyl-L-alanyl-L-alanine monomers provides a structure shown by Formula (I); or wherein said hydrogen bonding salt N-lauroyl-L-alanyl-L-alanine monomers provides a structure shown by Formula (II):

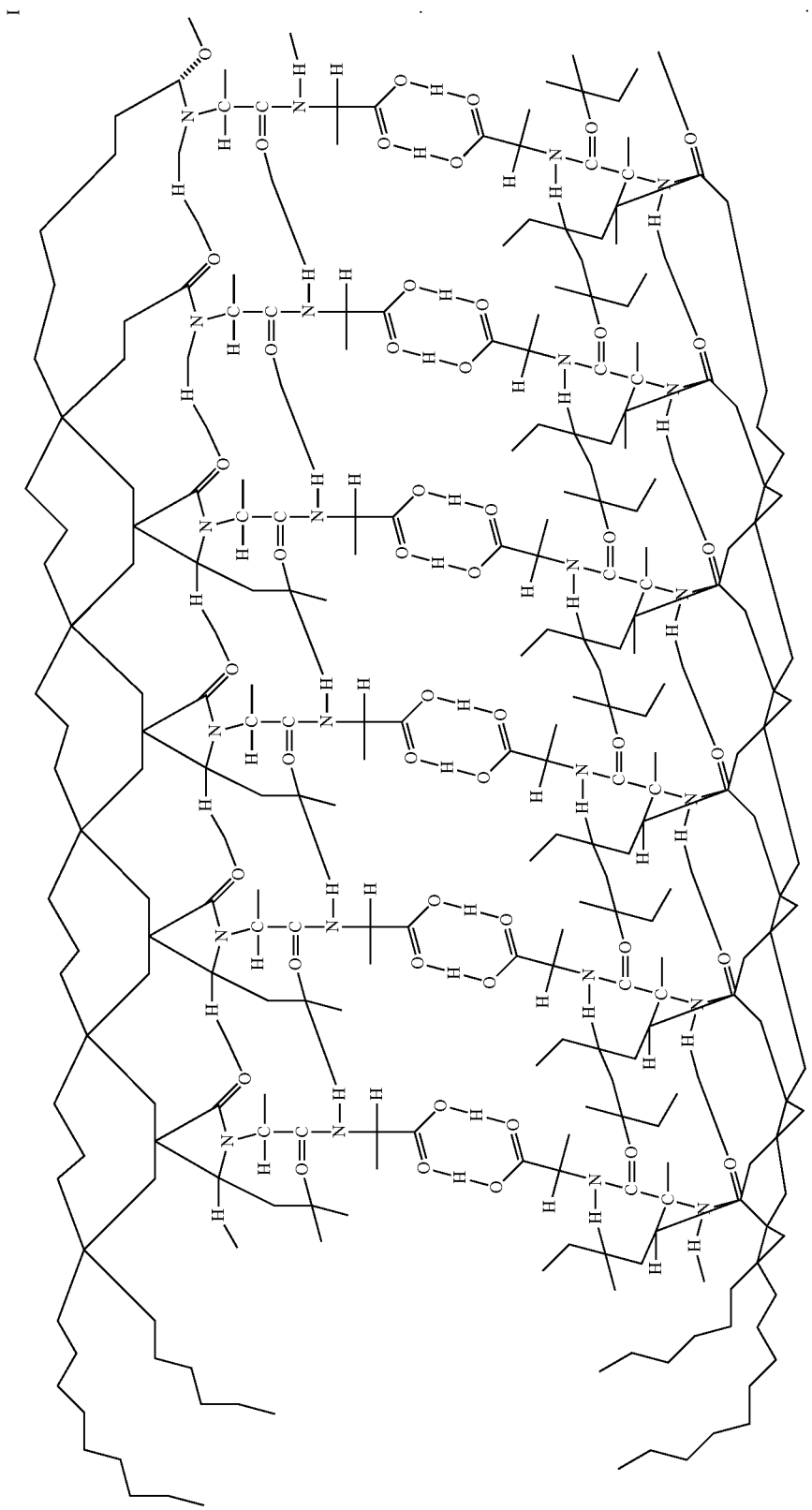

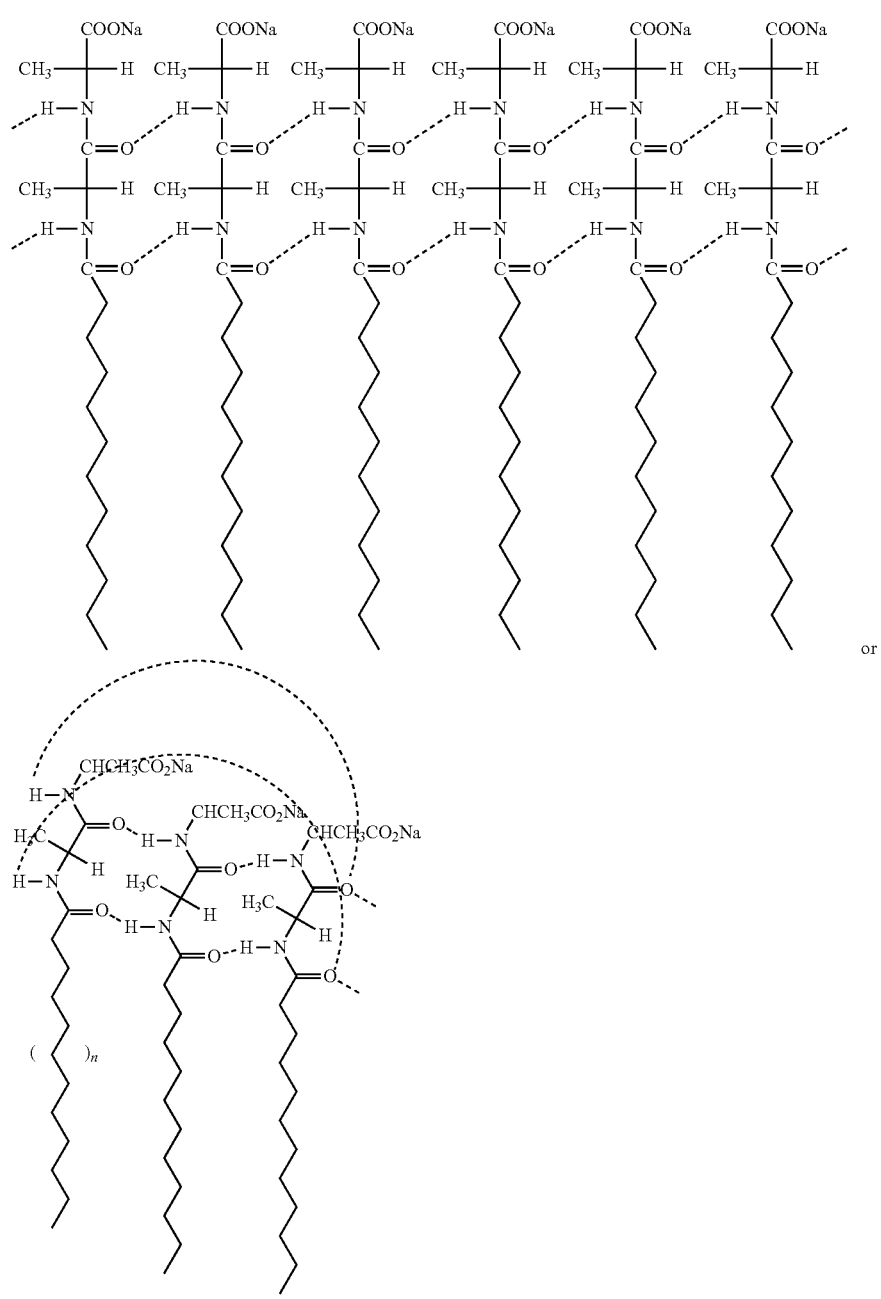

wherein n is 8-20,000; and wherein an n number of sodium N-lauroyl-L-alanyl-L-alanine molecules are linked in sequence by hydrogen bonds in the same plane, or an n number of sodium N-lauroyl-L-alanyl-L-alanine molecules are linked in sequence by hydrogen bonds and the first and last molecules are linked by hydrogen bonds to form a columnar structure.

3. The self-assembled amino acid supramolecular polymer or the salt thereof according to claim 1, wherein the polymer or the salt thereof has a weight average molecular weight of between 5000 and 5,000,000.

4. The self-assembled amino acid supramolecular polymer or the salt thereof according to claim 1, wherein the polymer or the salt thereof is substantially free or free of lauric acid.

5. A method for preparing the self-assembled amino acid supramolecular polymer or a salt thereof according to claim 1, comprising the following steps:
mixing a crude N-lauroyl-L-alanyl-L-alanine product, a solvent, L-alanyl-L-alanine and a catalyst, and stirring to obtain the self-assembled N-lauroyl-L-alanyl-L-alanine supramolecular polymer or the salt thereof according to claim 1.

6. The method according to claim 5, wherein the crude N-lauroyl-L-alanyl-L-alanine product is prepared with the following steps:
(1) dissolving L-alanyl-L-alanine and a metallic inorganic base in a mixed solution of distilled water and an organic solvent, and stirring uniformly to obtain an L-alanyl-L-alanine salt solution;

(2) adding lauroyl chloride and a metallic inorganic base in sequence to the L-alanyl-L-alanine salt solution obtained above, and then continuing the stirring to obtain a pasty N-lauroyl-L-alanyl-L-alanine salt;

(3) acidifying the pasty N-lauroyl-L-alanyl-L-alanine salt obtained above to precipitate a white solid gradually, cooling and then filtering to obtain the crude N-lauroyl-L-alanyl-L-alanine product.

7. The method according to claim 6, wherein, in Step (1), a molar ratio of the L-alanyl-L-alanine to the metallic inorganic base is 1:(1-1.5); the metallic inorganic base is selected from one or more of sodium hydroxide, potassium hydroxide, sodium carbonate, and potassium carbonate; and the organic solvent is selected from one or more of acetone, methanol, ethanol, acetonitrile, and tetrahydrofuran; and a volume ratio of the distilled water to the organic solvent is 1:(1-1.5).

8. The method according to claim 6, wherein, in Step (2), a feeding molar ratio of the lauroyl chloride to the L-alanyl-L-alanine is (0.8-1):1; the stirring is conducted under the following conditions: temperature 5-50° C., time 1-3 h; the metallic inorganic base has a concentration of 30-80%; and the metallic inorganic base is selected from one or more of sodium hydroxide, potassium hydroxide, sodium carbonate, and potassium carbonate.

9. The method according to claim 6, wherein the solvent is selected from acetone, methanol, ethanol, acetonitrile, tetrahydrofuran, and a mixed solvent comprising one or more of the above solvents and water; the catalyst is selected from one or more of sulfuric acid, p-toluenesulfonic acid, and an emulsifier; a molar ratio of the crude N-lauroyl-L-alanyl-L-alanine product, the solvent, L-alanyl-L-alanine, and the catalyst is 1:(5-10):(0.1-0.2):(0.001-0.1); and the stirring is conducted under the following conditions: temperature 25-100° C., pressure 5 kg-50 kg, time 1-3 h.

10. The method according to claim 6, wherein the crude N-lauroyl-L-alanyl-L-alanine product is prepared with the following steps:

(1) mixing and reacting N-lauroyl-L-alanine and a chlorinating reagent, cooling, adding pentan-2-one and activated carbon, conducting decolorization, filtration and reduced pressure distillation in sequence, and adding an organic solvent to dissolve acyl chloride in N-lauroyl-L-alanine to obtain an N-lauroyl-L-alanyl chloride solution;

(2) dissolving L-alanine and a metallic inorganic base in a mixed solution of distilled water and an organic solvent, and stirring uniformly to obtain an L-alanine salt solution;

(3) adding the N-lauroyl-L-alanyl chloride solution in acetone of (1) and a metallic inorganic base to the L-alanine salt solution of (2), and stirring to obtain a pasty N-lauroyl-L-alanyl-L-alanine salt;

(4) acidifying the pasty N-lauroyl-L-alanyl-L-alanine salt of (3) to precipitate a white solid gradually, cooling and then filtering to obtain the crude N-lauroyl-L-alanyl-L-alanine product.

11. The method according to claim 10, wherein, a molar ratio of the N-lauroyl-L-alanine to the chlorinating agent is (1-1.5):5, and the chlorinating agent is selected from one or more of thionyl chloride, phosphorus trichloride, triphosgene, and N-chlorosuccinimide.

12. A surfactant comprising the self-assembled amino acid supramolecular polymer or the salt thereof according to claim 1.

13. A surfactant comprising the sodium salt of the self-assembled amino acid supramolecular polymer according to claim 1.

14. The surfactant according to claim 13, wherein the surfactant is suitable for use in the field of daily chemicals, agriculture and pharmaceutical industry, or combination thereof.

15. A composition comprising (i) the self-assembled amino acid supramolecular polymer or the salt thereof according to claim 1 and (ii) a polymer formed by hydrogen bonding N-lauroyl-L-alanine monomers or a salt thereof, wherein the polymer formed by hydrogen bonding N-lauroyl-L-alanine monomers or the salt thereof is 0-60 wt. % based on a total weight of the composition.

16. An amino acid toothpaste comprising a friction agent, a humectant, a thickener and a surfactant, wherein the surfactant comprises the self-assembled amino acid supramolecular polymer or the salt thereof according to claim 1; wherein the toothpaste comprises 0.1-25 wt. % of the surfactant, 10-50 wt. % of the friction agent, 5-40 wt. % of the humectant, and 0.1-6 wt. % of the thickener, based on a total weight of the toothpaste.

17. A skin care composition comprising, based on total weight of the composition:

| | |
|---|---|
| Oil | 50-95% by weight |
| Surfactant | 0.5-30% by weight; and |
| Suspended particles | 0-45% by weight | wherein the surfactant comprises an amino acid surfactant that comprises the self-assembled amino acid supramolecular polymer or the salt thereof according to claim 1.

18. An amino acid laundry liquid comprising a surfactant, wherein the surfactant comprises an amino acid surfactant that comprises the self-assembled amino acid supramolecular polymer or the salt thereof according to claim 1; wherein the surfactant has a weight percentage of 0.1-25% based on total weight of the laundry liquid.

* * * * *